US009394574B2

(12) United States Patent
Winchell et al.

(10) Patent No.: US 9,394,574 B2

(45) Date of Patent: Jul. 19, 2016

(54) **METHODS FOR DETECTING *LEGIONELLA* NUCLEIC ACIDS IN A SAMPLE**

(71) Applicant: The United States of America as represented by the Secretary of the Department of Health and Human Services, Washington, DC (US)

(72) Inventors: Jonas M. Winchell, Lilburn, GA (US); Alvaro J. Benitez, Kennesaw, GA (US)

(73) Assignee: The United States of America as represented by the Secretary of the Department of Health and Human Services, Washington, DC (US)

( * ) Notice: Subject to any disclaimer, the term of this patent is extended or adjusted under 35 U.S.C. 154(b) by 25 days.

(21) Appl. No.: 13/895,898

(22) Filed: May 16, 2013

(65) Prior Publication Data

US 2013/0331285 A1 Dec. 12, 2013

Related U.S. Application Data

(63) Continuation-in-part of application No. PCT/US2013/030217, filed on Mar. 11, 2013.

(60) Provisional application No. 61/658,627, filed on Jun. 12, 2012.

(51) Int. Cl.
*C12P 19/34* (2006.01)
*C12Q 1/68* (2006.01)

(52) U.S. Cl.
CPC ............ *C12Q 1/689* (2013.01); *C12Q 2600/16* (2013.01)

(58) Field of Classification Search
USPC ...................................... 435/6.11, 6.12, 91.2
See application file for complete search history.

(56) References Cited

U.S. PATENT DOCUMENTS

| | | | | |
|---|---|---|---|---|
| 7,659,388 | B2 | 2/2010 | Oh et al. | |
| 7,794,944 | B2 | 9/2010 | Felden | |
| 7,972,777 | B1 | 7/2011 | Barry et al. | |
| 2005/0118625 | A1 | 6/2005 | Mounts | |
| 2008/0081770 | A1 | 4/2008 | Oh et al. | |
| 2009/0092969 | A1* | 4/2009 | Aye et al. | 435/6 |

FOREIGN PATENT DOCUMENTS

| | | |
|---|---|---|
| CN | 101 851 652 | 10/2010 |
| EP | 0943691 | 9/1999 |
| EP | 1179090 | 4/2010 |
| JP | 2009225793 | 10/2009 |
| WO | WO 03/095677 | 11/2003 |
| WO | WO 2009/048873 | 4/2009 |
| WO | WO 2011/020926 | 2/2011 |
| WO | WO 2011/133433 | 10/2011 |
| WO | WO 2013/187958 | 12/2013 |

OTHER PUBLICATIONS

Rychlik et al., Nucleic Acids Research 17(21), 8543-8551 (1989).*

Benitez et al., "Clinical application of a multiplex real-time PCR assay for simultaneous detection of *Legionella* species, *Legionella pneumophila*, and *Legionella pneumophila* serogroup 1," *Journal of Clinical Microbiology*, vol. 51, No. 1, pp. 348-351, 2013.

Su et al., "Identification of legionella species by use of an oligonucleotide array," *Journal of Clinical Microbiology*, vol. 47, No. 5, pp. 1386-1392, 2009.

Templeton et al., "Development and clinical evaluation of an internally controlled single-tube multiplex real-time PCR assay for detection of *Legionella pneumophila* and other *Legionella* species," *Journal of Clinical Microbiology*, vol. 41, No. 9, pp. 4016-4021, 2003.

Degtyar et al., "A *Legionella* effector acquired from protozoa is involved in sphingolipids metabolism and is targeted to the host cell mitochondria," *Cellular Microbiology*, vol. 11, No. 8, pp. 1219-1235, 2009.

Feldman et al., "A Specific Genomic Location within the *icm/dot* Pathogenesis Region of Different *Legionella* Species Encodes Functionally Similar but Nonhomologous Virulence Proteins," *Infection and Immunity*, vol. 72, No. 8, pp. 4503-4511, 2004.

Feldman et al., "Coevolution between nonhomologous but functionally similar proteins and their conserved partners in the *Legionella* pathogenesis system," *PNAS*, vol. 102, No. 34, pp. 12206-12211, 2005.

Su et al, "Identification of *Legionella* Species by Use of an Oligonucleotide Array," *Journal of Clinical Microbiology*, vol. 47, No. 5, pp. 1386-1392, 2009.

Zhou et al., "PCR methods for the rapid detection and identification of four pathogenic *Legionella* spp. and two *Legionella pneumophila* subspecies based on the gene amplification of *gyrB*," *App. Microbiol. Biotechnol.*, vol. 91, pp. 777-787, 2011.

Benitez and Winchell, "Rapid Detection and Speciation of Pathogenic Non-pneumophila *Legionella* Species Using a Multiplex Real-time PCR Assay," 113$^{th}$ General Meeting of the American Society for Microbiology, May 18-21, 2013 (Abstract, 1 page).

(Continued)

*Primary Examiner* — Kenneth Horlick

(74) *Attorney, Agent, or Firm* — Klarquist Sparkman, LLP

(57) ABSTRACT

Methods for detecting *Legionella* (such as *Legionella* spp., *Legionella pneumophila, Legionella pneumophila* serogroup 1, *Legionella bozemanii, Legionella dumoffii, Legionella feeleii, Legionella longbeachae*, and/or *Legionella micdadei*) are disclosed. A sample suspected of containing one or more *Legionella* nucleic acids is screened for the presence or absence of that nucleic acid. Determining whether *Legionella* nucleic acid is present in the sample can be accomplished by contacting the sample with detectably labeled probes capable of hybridizing to a *Legionella* nucleic acid and detecting hybridization between the probes and nucleic acids in the sample. Detection of hybridization indicates that a *Legionella* nucleic acid is present in the sample. Also disclosed are probes and primers for the detection of *Legionella*, and kits that contain the disclosed probes and/or primers.

6 Claims, 7 Drawing Sheets

(56) References Cited

OTHER PUBLICATIONS

Benitez and Winchell, "Clinical Application of a Multiplex Real-time PCR Assay for Simultaneous Detection of *Legionella* Species, *Legionella pneumophila*, and *Legionella pneumophila* serogroup 1," *J. Clin. Microbiol.*, vol. 51, pp. 348-351, 2013.
Merault et al., "Specific Real-time PCR for Simultaneous Detection and Identification of *Legionella pneumophila* Serogroup 1 in Water and Clinical Samples," *Appl. Environ. Microbiol.*, vol. 77, pp. 1708-1717, 2011.
Ratcliff et al., "Sequence-Based Classification Scheme for the Genus *Legionella* Targeting the *mip* Gene," *J. Clin. Microbiol.*, vol. 36, pp. 1560-1567, 1998.
Stolhaug and Bergh, "Identification and Differentiation of *Legionella pneumophila* and *Legionella* spp. with Real-time PCR Targeting the 16S rRNA Gene and Species Identification by *mip* Sequencing," *Appl. Environ. Microbiol.*, vol. 72, pp. 6394-6398, 2006.

* cited by examiner

SEQUENCE LISTING

```
<160> NUMBER OF SEQ ID NOS: 36

<210> SEQ ID NO 1
<211> LENGTH: 708
<212> TYPE: DNA
<213> ORGANISM: Legionella pneumophila

<400> SEQUENCE: 1

ttgtttatga agatgaaatt ggtgactgcg gctgttatgg ggcttgcaat gtcaacagca     60

atggctgcaa ccgatgccac atcattagct acagacaagg ataagttgtc ttatagcatt    120

ggtgccgatt tggggaagaa ttttaaaaat caaggcatag atgttaatcc ggaagcaatg    180

gctaaaggca tgcaagacgc tatgagtggc gctcaattgg ctttaaccga acagcaaatg    240

aaagacgttc ttaacaagtt tcagaaagat ttgatggcaa agcgtactgc tgaattcaat    300

aagaaagcgg atgaaaataa agtaaaaggg gaagcctttt taactgaaaa caaaaacaag    360

ccaggcgttg ttgtattgcc aagtggtttg caatacaaag taatcaatgc tggaaatggt    420

gttaaacccg gtaaatcgga tacagtcact gtcgaataca ctggtcgtct gattgatggt    480

accgtttttg acagtaccga aaaaactggt aagccagcaa cttttcaggt ttcacaagtt    540

atcccaggat ggacagaagc tttgcaattg atgccagctg gatcaacttg ggaaatttat    600

gttccctcag gtcttgcata tggcccacgt agcgttggcg gacctattgg cccaaatgaa    660
```

-continued actttaatat ttaaaattca cttaatttca gtgaaaaaat catcttaa 708

<210> SEQ ID NO 2
<211> LENGTH: 637
<212> TYPE: DNA
<213> ORGANISM: Legionella pneumophila

<400> SEQUENCE: 2
aaacaggact tgcgcccccc aatcctctcg gtaaaacatt ttttgccttg accttggggt 60
tttccgtaag tcctgaaaat atattcggta tgctggcggg attttgctta catgccggca 120
ttttatgtta taattaaagt gtacagaatg gggggcgacc tggcttcgac gtgggttgca 180
aaaccggaag tgcatgccga gaaggagatc tctcgtaaat aagactcaat taaatataaa 240
tgcaaacgat gaaaactttg ctggtgggga agctatcgct gcctaataag cactttagtt 300
aaaccatcac tgtgtactgg ccaataaacc cagtatcccg ttcgaccgag cccgcttatc 360
ggtatcgaat caacggtcat aagagataag ctagcgtcct aatctatccc gggttatggc 420
gcgaaactca gggaatcgct gtgtatcatc ctgcccgtcg gaggagccac agttaaattc 480
aaaagacaag gctatgcatg tagagctaaa ggcagaggac ttgcggacgc gggttcgatt 540
cccgccgcct ccaccaattc attatccgat acagtccaat accgggtctt tcccaaatac 600
ctgaatcttc tacacatctt gtttattcca aacaaac 637

<210> SEQ ID NO 3
<211> LENGTH: 852
<212> TYPE: DNA
<213> ORGANISM: Legionella pneumophila

<400> SEQUENCE: 3
atgacctcaa tatcctcaaa aactcagacg tttaaagaaa cagtagtcta tggagttgat 60
aagtttaggc ttttagctgt tttaagaaat atatgggatt accgcttgct tttatggatt 120
ttttgtaaac gagatctcaa agggcgttac agtcaaacca tcttgggatt gggttgggtt 180
attttaactc ctttgattac ggttggggtg tttgtcattg tttttggcat catgataaag 240
gtacctaccg atgggctgcc tactgtcatg ttctatttgg ttgcggttat accttggtat 300
tcctttttaa atgttctcaa cccttccata caaatgattg agggaaatgc ttcgttaata 360
acaaaggtct attttccaag agcgttgata ggcggtgcct atgctatggg agctgcggtt 420
gattttctga tggcttatgt gtttttgata accccctttg caatttatta tggcctttgg 480
tctatcaagt tattaattat tatgccattc ctgctgatat ctaccttaat gattggatta 540
ggtattggtt tggttttagc acctatcaat gcaaaatata gggatattaa acattttatg 600
cctctggctt tgcagttatt ttattactcc actccagcga tttaccctgt ttctgctgtg 660
cctgtgtggg ctaaaccatg gtatgctgtt aatccattat ctcttgttat caccagttat 720
cgagaggtgt taatggggca ttggccatca cctactataa taatgacatt atctggtatg 780
gcaattataa ctttccttgt ggggcttgtt gcatttcatc acatggagca taaggtagtt 840
gatattttat ga 852

<210> SEQ ID NO 4
<211> LENGTH: 14
<212> TYPE: DNA
<213> ORGANISM: Artificial Sequence
<220> FEATURE:
<223> OTHER INFORMATION: Synthetic oligonucleotide primer

<400> SEQUENCE: 4

-continued ggcgacctgg cttc 14

<210> SEQ ID NO 5
<211> LENGTH: 24
<212> TYPE: DNA
<213> ORGANISM: Artificial Sequence
<220> FEATURE:
<223> OTHER INFORMATION: Synthetic oligonucleotide primer

<400> SEQUENCE: 5
ggtcatcgtt tgcatttata ttta 24

<210> SEQ ID NO 6
<211> LENGTH: 12
<212> TYPE: DNA
<213> ORGANISM: Artificial Sequence
<220> FEATURE:
<223> OTHER INFORMATION: Synthetic oligonucleotide probe

<400> SEQUENCE: 6
cgtgggttgc aa 12

<210> SEQ ID NO 7
<211> LENGTH: 22
<212> TYPE: DNA
<213> ORGANISM: Artificial Sequence
<220> FEATURE:
<223> OTHER INFORMATION: Synthetic oligonucleotide primer

<400> SEQUENCE: 7
ttgtcttata gcattggtgc cg 22

<210> SEQ ID NO 8
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 8
ccaattgagc gccactcata g 21

<210> SEQ ID NO 9
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 9
cggaagcaat ggctaaaggc atgca 25

<210> SEQ ID NO 10
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 10
tgcctctggc tttgcagtta 20

<210> SEQ ID NO 11
<211> LENGTH: 21
<212> TYPE: DNA

-continued

<213> ORGANISM: Artificial Sequence
<220> FEATURE:
<223> OTHER INFORMATION: Synthetic oligonucleotide primer

<400> SEQUENCE: 11
cacacaggca cagcagaaac a 21

<210> SEQ ID NO 12
<211> LENGTH: 22
<212> TYPE: DNA
<213> ORGANISM: Artificial Sequence
<220> FEATURE:
<223> OTHER INFORMATION: Synthetic oligonucleotide probe

<400> SEQUENCE: 12
tttattactc cactccagcg at 22

<210> SEQ ID NO 13
<211> LENGTH: 625
<212> TYPE: DNA
<213> ORGANISM: Legionella bozemanii

<400> SEQUENCE: 13
ggacgaggga tacccgtcga tattcataaa gaagaaggac gatccgctgc tgaagtgatt 60
atgacagtgc ttcacgccgg tggtaaattt gatgataatt cttataaagt atcgggtggt 120
ttgcatggag tgggtgtttc tgtagttaat gccttatccg aggaattaca tttaaccgta 180
cgtcgtcatg gtaaaatcca tgagcaacat taccgtaatg gagttccaga tgcgccaatg 240
gcagaaacag gagatgcatc gacaaccgga actcaaattt ggtttaaacc aagtgccgaa 300
acgttttcta atattgagtt tcactatgat attttagcaa aacggctaag agaattatct 360
tatttaaatt caggtgtttg catccattta ttcgatgagc gatcccaaag gcaagacact 420
tttcattatg aaggtggaat cacggcattt gtggagcatc tcaataaaaa taaaaatact 480
attatgccca ctgtttttc tatgaccgct gaaaaagata acattgttgt tgaactgtct 540
atgcagtgga atgattctta tcaagaaaca ctttattgct ttacaaataa tatccctcag 600
cgtgacggtg gaacacatat ggctg 625

<210> SEQ ID NO 14
<211> LENGTH: 1794
<212> TYPE: DNA
<213> ORGANISM: Legionella dumoffii

<400> SEQUENCE: 14
atgtttactt tcattaccgg actcctaaat agtggacttg aagcattcga tgaaacattt 60
aaagataccc cagcccataa gatcgttttt gcgacagcag cactttattt tatttggcaa 120
cagtacccta caataacgca ggcctatcgt tcccgaaaca acaccacttt gaaacagcgt 180
ttaattgaca tagcctacag tttgggcaaa aatttaccac cagtaaaatc ctacttggat 240
aaggaactga ataaagatct gcagaacact aaagacaaat taaaggaatt acgtgcacaa 300
atgaccctcc aagataaaat tcctgaaaaa aagacacccg caattttcct tttaaaagaa 360
tttggtatag ctccggaaga atgtcttttt aattttgctg gtataaaaga gggagacgag 420
gccaggcgat ttactgttaa ggaaggagat gggaaggatt caggtgcgct ttatgcagtt 480
catccccggg aacttaccga attacttaaa gaggtctatg caaaaagttc tttaatcaat 540
cccctgcacg ataaatggcc acggattgtt gccatgcagg ctgagattat tcgctggtgc 600
caggatttat ttggcggctc taaagaagct tatggactta tcacccatgg aggtacgaca 660

```
agtattattg aagccatggc tgcttatgtc actcatgcac gggcgaaagg aattaaaaat    720

cctgaaattg tggtaccgga aacagcacac gcagcattta aaaaagcagc tgatttgacc    780

ggtgcccgat tgattaccgt tccagttgat ccaaaatccg gtgctgttaa cgcacatgta    840

atgagaaaat acatttcggg caatactgcc gtaattgtgg gatcagctcc ctctttcatg    900

tatggtgtaa atgatccaat ccctgagtta gggaaggtag ctcaggaatt gggtgtccca    960

ttgcatgtag atgcatgctt gggtggattt ttaactgcat ttctggagac ttctaaaact   1020

cctatggatt ttcgcgtgaa aggggttact tccatatcag cagatttgca caaatacggt   1080

aattgcccta aaggcacttc tgtttgcctt tttagtgaag actcccctgt tttatcagta   1140

tatgctgcgc taaactggtc aggcgggctt tatactactc ccggtatttt agacggttca   1200

accagcgggg cacgggttgc agaaatatat accactctct cctattacgg acgtaaacaa   1260

tatcaggaaa tctccaggag tattataaca atgcgccaac gtctgcaaga caaggttgcc   1320

gaactctata aacctgatgc atcaggaaag cgcgacatct atatttttgg aaaccctcaa   1380

tggtccgttc tgggtttccg gagtgatact ttgaaccctc attttattgc gaacgagctg   1440

gataagcgcg gttggaaact gaattcacta caaaaacctg atggattcca tttgtgcttg   1500

actcatgtgc atactttagt tgatcgcttt gaagataaat ttattaaaga cctgcaagag   1560

tcgatagagg ccgtgaagca atatcccgct gacaaaaaac ctgagggtaa cgttaaagtc   1620

tatggaacca taggaatact gcctacccaa gtacaagaag taatatgccg acaataccaa   1680

agagcccgcc tatattatga agcgacatgt acccaattag gatttttctc aaccccagac   1740

agacaagaga ataaaatgga tatttccgaa gaaaagaaag aactcacctt ataa         1794
```

<210> SEQ ID NO 15
<211> LENGTH: 216
<212> TYPE: DNA
<213> ORGANISM: Legionella feeleii

<400> SEQUENCE: 15

```
atgggccttg gctttttga taataaaaaa ccgactatca atgcagatga agtaagggct      60

aacattgctc ttataaaccg gtttatcggt cttttagata aagcgagtga taatccatca    120

aattctcaag ctcgagacaa gctggttgat ctcggcaaca aacttgggga agcactcgag    180

caacctgaaa taacggaatc taaaaaatta acataa                              216
```

<210> SEQ ID NO 16
<211> LENGTH: 267
<212> TYPE: DNA
<213> ORGANISM: Legionella longbeachae

<400> SEQUENCE: 16

```
atggcatatg cgaaaggttt ttttagcgtg tcttcaagtt ctgcgaatga aacaagtgat     60

gagaaggcca ctaccgaaga tgccgcattt ttggccaata ctcttgaagc attggaaaag    120

cgaatcactc aaataatgaa agtgaaaata caaacccaaa atactgcaga agttgctgat    180

tgtgagagcg caattcaaca attagaaaag tgtcgccaag aagttgtatc tcatgctcag    240

ataagtcatt cgccacgtcc ttggtag                                        267
```

<210> SEQ ID NO 17
<211> LENGTH: 363
<212> TYPE: DNA
<213> ORGANISM: Legionella micdadei

<400> SEQUENCE: 17
atgttgcgca atccgtatac gcattttaaa ttgacaagtg agagcaagag ttcagcgaca 60
gatttgcttt ccagttcttc cccgacagaa ggagaacctt ccggtgtgcc tatcgctgtc 120
ggaatagata cattacatag tttgcaaagg ttaaatagtc agaccgataa aatgatggcg 180
attagtaaga ctccagggaa tatgactgca tctgcaacgt taggtaaagc acttaaaagg 240
actggaagcg ctatcaataa tgaatttcct aaagagattc aagaagttca aatggctcaa 300
gcagaatcaa gtcatgattc gtcccccgaa gaaactacat ctgtaagctt ttcaaggccc 360
taa 363

<210> SEQ ID NO 18
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 18
tccgctgctg aagtgattat g 21

<210> SEQ ID NO 19
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 19
catgcaaacc acccgatact 20

<210> SEQ ID NO 20
<211> LENGTH: 24
<212> TYPE: DNA
<213> ORGANISM: Artificial Sequence
<220> FEATURE:
<223> OTHER INFORMATION: Synthetic oligonucleotide probe

<400> SEQUENCE: 20
gtgcttcacg ccggtggtaa attt 24

<210> SEQ ID NO 21
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 21
caggaaagcg cgacatctat 20

<210> SEQ ID NO 22
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 22
atccagctcg ttcgcaataa 20

<210> SEQ ID NO 23
<211> LENGTH: 24

<212> TYPE: DNA
<213> ORGANISM: Artificial Sequence
<220> FEATURE:
<223> OTHER INFORMATION: Synthetic oligonucleotide probe

<400> SEQUENCE: 23
tggaaaccct caatggtccg ttct 24

<210> SEQ ID NO 24
<211> LENGTH: 19
<212> TYPE: DNA
<213> ORGANISM: Artificial Sequence
<220> FEATURE:
<223> OTHER INFORMATION: Synthetic oligonucleotide primer

<400> SEQUENCE: 24
aaccggttta tcggtcttt 19

<210> SEQ ID NO 25
<211> LENGTH: 18
<212> TYPE: DNA
<213> ORGANISM: Artificial Sequence
<220> FEATURE:
<223> OTHER INFORMATION: Synthetic oligonucleotide primer

<400> SEQUENCE: 25
atcaaccagc ttgtctcg 18

<210> SEQ ID NO 26
<211> LENGTH: 30
<212> TYPE: DNA
<213> ORGANISM: Artificial Sequence
<220> FEATURE:
<223> OTHER INFORMATION: Synthetic oligonucleotide probe

<400> SEQUENCE: 26
gcgagtgata atccatcaaa ttctcaagct 30

<210> SEQ ID NO 27
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 27
ctgcagaagt tgctgattgt g 21

<210> SEQ ID NO 28
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 28
gacgtggcga atgacttatc t 21

<210> SEQ ID NO 29
<211> LENGTH: 27
<212> TYPE: DNA
<213> ORGANISM: Artificial Sequence
<220> FEATURE:
<223> OTHER INFORMATION: Synthetic oligonucleotide probe

<400> SEQUENCE: 29
tgtcgccaag aagttgtatc tcatgct 27

<210> SEQ ID NO 30
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 30
tgacaagtga gagcaagagt t 21

<210> SEQ ID NO 31
<211> LENGTH: 23
<212> TYPE: DNA
<213> ORGANISM: Artificial Sequence
<220> FEATURE:
<223> OTHER INFORMATION: Synthetic oligonucleotide primer

<400> SEQUENCE: 31
gtatctattc cgacagcgat agg 23

<210> SEQ ID NO 32
<211> LENGTH: 24
<212> TYPE: DNA
<213> ORGANISM: Artificial Sequence
<220> FEATURE:
<223> OTHER INFORMATION: Synthetic oligonucleotide probe

<400> SEQUENCE: 32
acagaaggag aaccttccgg tgtg 24

<210> SEQ ID NO 33
<211> LENGTH: 24
<212> TYPE: DNA
<213> ORGANISM: Artificial Sequence
<220> FEATURE:
<223> OTHER INFORMATION: Synthetic oligonucleotide probe

<400> SEQUENCE: 33
tgcttcacgc cggtggtaaa tttg 24

<210> SEQ ID NO 34
<211> LENGTH: 30
<212> TYPE: DNA
<213> ORGANISM: Artificial Sequence
<220> FEATURE:
<223> OTHER INFORMATION: Synthetic oligonucleotide probe.

<400> SEQUENCE: 34
agcgagtgat aatccatcaa attctcaagc 30

<210> SEQ ID NO 35
<211> LENGTH: 24
<212> TYPE: DNA
<213> ORGANISM: Artificial Sequence
<220> FEATURE:
<223> OTHER INFORMATION: Synthetic oligonucleotide probe

<400> SEQUENCE: 35
aaatttacca ccggcgtgaa gcac 24

<210> SEQ ID NO 36
<211> LENGTH: 30
<212> TYPE: DNA
<213> ORGANISM: Artificial Sequence -continued

```
<220> FEATURE:
<223> OTHER INFORMATION: Synthetic oligonucleotide probe

<400> SEQUENCE: 36

agcttgagaa tttgatggat tatcactcgc                              30
```

METHODS FOR DETECTING *LEGIONELLA* NUCLEIC ACIDS IN A SAMPLE

CROSS REFERENCE TO RELATED APPLICATIONS

This is a continuation-in-part of International Application No. PCT/US2013/030217, filed Mar. 11, 2013, which claims the benefit of U.S. Provisional Application No. 61/658,627, filed Jun. 12, 2012, both of which are incorporated herein by reference in their entirety.

FIELD

This disclosure concerns methods and compositions related to the detection of *Legionella*, particularly utilizing multiplex real-time PCR.

BACKGROUND

Legionellae account for about 2-8% of atypical community-acquired pneumonia cases. Legionellosis is caused predominantly (in about 70% of all cases) by *Legionella pneumophila* serogroup 1 (Sg1), although other serogroups (for example, Sg2, 4, and 6) and other species (such as *L. bozemanii, L. longbeachae, L. dumoffii, L. feeleii*, and *L. micdadei*) have been reported as disease causing agents.

Currently, culture is the standard for identification of *Legionella* in both clinical and environmental samples. Detection by culture is not an effective strategy for diagnosis or surveillance, as these agents require specific media and expertise, and thus culture identification can take weeks. Thus, there is a need for rapid, sensitive, high-throughput test for detection of *Legionella* to aid in diagnosis, routine surveillance, and identification of the source of an outbreak.

SUMMARY

Disclosed herein are methods for detecting and/or discriminating presence of one or more *Legionella* nucleic acids in a sample, such as a biological or environmental sample. The disclosed methods can be used to diagnose an infection with *Legionella* in a subject or to detect presence of *Legionella* in an environmental sample, such as a water sample. The disclosed methods can also discriminate whether one or more of *Legionella pneumophila, Legionella pneumophila* serogroup 1, *L. bozemanii, L. dumoffii, L. feeleii, L. longbeachae*, or *L. micdadei* is present in the sample or the subject. The disclosed methods provide rapid, sensitive, and specific detection and/or discrimination of *Legionella* nucleic acids, for example, utilizing real-time PCR (such as multiplex real-time PCR).

In some embodiments, the disclosed methods involve contacting a sample with one or more probes capable of hybridizing to a *Legionella* nucleic acid, such as one or more of a *Legionella* spp. ssrA nucleic acid (such as SEQ ID NO: 2), a *Legionella pneumophila* mip nucleic acid (such as SEQ ID NO: 1), a *Legionella pneumophila* serogroup 1 wzm nucleic acid (such as SEQ ID NO: 3), a *Legionella bozemanii* gyrB nucleic acid (such as SEQ ID NO: 13), a *Legionella dumoffii* legS2 nucleic acid (such as SEQ ID NO: 14), a *Legionella feeleii* figA nucleic acid (such as SEQ ID NO: 15), a *Legionella longbeachae* ligB nucleic acid (such as SEQ ID NO: 16), or a *Legionella micdadei* migB nucleic acid (such as SEQ ID NO: 17) under high or very high stringency conditions, wherein each of the probes are detectably labeled, and detecting hybridization between one or more of the probes and a nucleic acid. Detection of hybridization of the *Legionella* spp. ssrA probe indicates the presence of *Legionella* spp. nucleic acid in the sample, detection of hybridization of the *Legionella pneumophila* mip probe indicates the presence of *Legionella pneumophila* nucleic acid in the sample, detection of hybridization of the *Legionella pneumophila* serogroup 1 wzm probe indicates the presence of *Legionella pneumophila* serogroup 1 nucleic acid in the sample, detection of hybridization of the *Legionella bozemanii* gyrB probe indicates presence of *Legionella bozemanii* nucleic acid in the sample, detection of hybridization of the *Legionella dumoffii* legS2 probe indicates presence of *Legionella dumoffii* nucleic acid in the sample, detection of hybridization of the *Legionella feeleii* figA probe indicates presence of *Legionella dumoffii* nucleic acid in the sample, detection of hybridization of the *Legionella longbeachae* ligB probe indicates presence of *Legionella longbeachae* nucleic acid in the sample, and detection of hybridization of the *Legionella micdadei* migB probe indicates presence of *Legionella longbeachae* nucleic acid in the sample.

In specific embodiments, the probe capable of hybridizing to *Legionella* spp. ssrA nucleic acid includes or consists essentially of a nucleic acid sequence at least 90% identical to that set forth as SEQ ID NO: 6, the probe capable of hybridizing to *Legionella pneumophila* mip nucleic acid includes or consists essentially of a nucleic acid sequence at least 90% identical to that set forth as SEQ ID NO: 9, the probe capable of hybridizing to *Legionella pneumophila* serogroup 1 wzm nucleic acid includes or consists essentially of a nucleic acid sequence at least 90% identical to that set forth as SEQ ID NO: 12, the probe capable of hybridizing to *Legionella bozemanii* gyrB nucleic acid includes or consists essentially of a nucleic acid sequence at least 90% identical to that set forth as SEQ ID NO: 20, SEQ ID NO: 33, or SEQ ID NO: 35, the probe capable of hybridizing to *Legionella dumoffii* legS2 nucleic acid includes or consists essentially of a nucleic acid sequence at least 90% identical to that set forth as SEQ ID NO: 23, the probe capable of hybridizing to *Legionella feeleii* figA nucleic acid includes or consists essentially of a nucleic acid sequence at least 90% identical to that set forth as SEQ ID NO: 26, SEQ ID NO: 34, or SEQ ID NO: 36, the probe capable of hybridizing to *Legionella longbeachae* ligB nucleic acid includes or consists essentially of a nucleic acid sequence at least 90% identical to that set forth as SEQ ID NO: 29, and the probe capable of hybridizing to *Legionella micdadei* migB nucleic acid includes or consists essentially of a nucleic acid sequence at least 90% identical to that set forth as SEQ ID NO: 32, or the reverse complement of any thereof. In specific embodiments, the disclosed probes are detectably labeled. In some examples, the probes are labeled with a donor fluorophore and an acceptor fluorophore.

In some embodiments, the disclosed methods include amplifying one or more *Legionella* nucleic acids, such as a *Legionella* spp. ssrA nucleic acid (such as SEQ ID NO: 2 or a portion thereof), a *Legionella pneumophila* mip nucleic acid (such as SEQ ID NO: 1 or a portion thereof), or a *Legionella pneumophila* serogroup 1 wzm nucleic acid (such as SEQ ID NO: 3 or a portion thereof). In some examples, a primer specific for *Legionella* spp. nucleic acid includes a nucleic acid sequence at least 90% identical to SEQ ID NO: 4 or SEQ ID NO: 5, or the reverse complement thereof. In other examples, a primer specific for *Legionella pneumophila* mip nucleic acid includes a nucleic acid sequence at least 90% identical to SEQ ID NO: 7 or SEQ ID NO: 8, or the reverse complement thereof. In additional examples, a primer specific for *Legionella pneumophila* serogroup 1 wzm nucleic acid includes a nucleic acid sequence at least 90% identical to SEQ ID NO: 10 or SEQ ID NO: 11, or the reverse complement thereof.

In additional embodiments, the disclosed methods include amplifying one or more *Legionella* nucleic acids, such as a *Legionella bozemanii* nucleic acid (such as SEQ ID NO: 13 or a portion thereof), a *Legionella dumoffii* legS2 nucleic acid (such as SEQ ID NO: 14 or a portion thereof), a *Legionella feeleii* figA nucleic acid (such as SEQ ID NO: 15 or a portion thereof), a *Legionella longbeachae* ligB nucleic acid (such as SEQ ID NO: 16 or a portion thereof), or a *Legionella micdadei* migB nucleic acid (such as SEQ ID NO: 17 or a portion thereof). In some examples, a primer specific for *Legionella bozemanii* gyrB nucleic acid includes a nucleic acid sequence at least 90% identical to SEQ ID NO: 18 or SEQ ID NO: 19, or the reverse complement thereof. In additional examples, a primer specific for *Legionella dumoffii* legS2 nucleic acid includes a nucleic acid sequence at least 90% identical to SEQ ID NO: 21 or SEQ ID NO: 22, or the reverse complement thereof. In additional examples, a primer specific for *Legionella feeleii* figA nucleic acid includes a nucleic acid sequence at least 90% identical to SEQ ID NO: 24 or SEQ ID NO: 25, or the reverse complement thereof. In additional examples, a primer specific for *Legionella longbeachae* ligB nucleic acid includes a nucleic acid sequence at least 90% identical to SEQ ID NO: 27 or SEQ ID NO: 28, or the reverse complement thereof. In additional examples, a primer specific for *Legionella micdadei* migB nucleic acid includes a nucleic acid sequence at least 90% identical to SEQ ID NO: 30 or SEQ ID NO: 31, or the reverse complement thereof.

This disclosure also provides kits for detecting one or more of *Legionella* nucleic acids in a biological sample, for example, including one or more of the probes and primers disclosed herein.

The foregoing and other features of the disclosure will become more apparent from the following detailed description, which proceeds with reference to the accompanying figures.

SEQUENCE LISTING

Figure 1A:
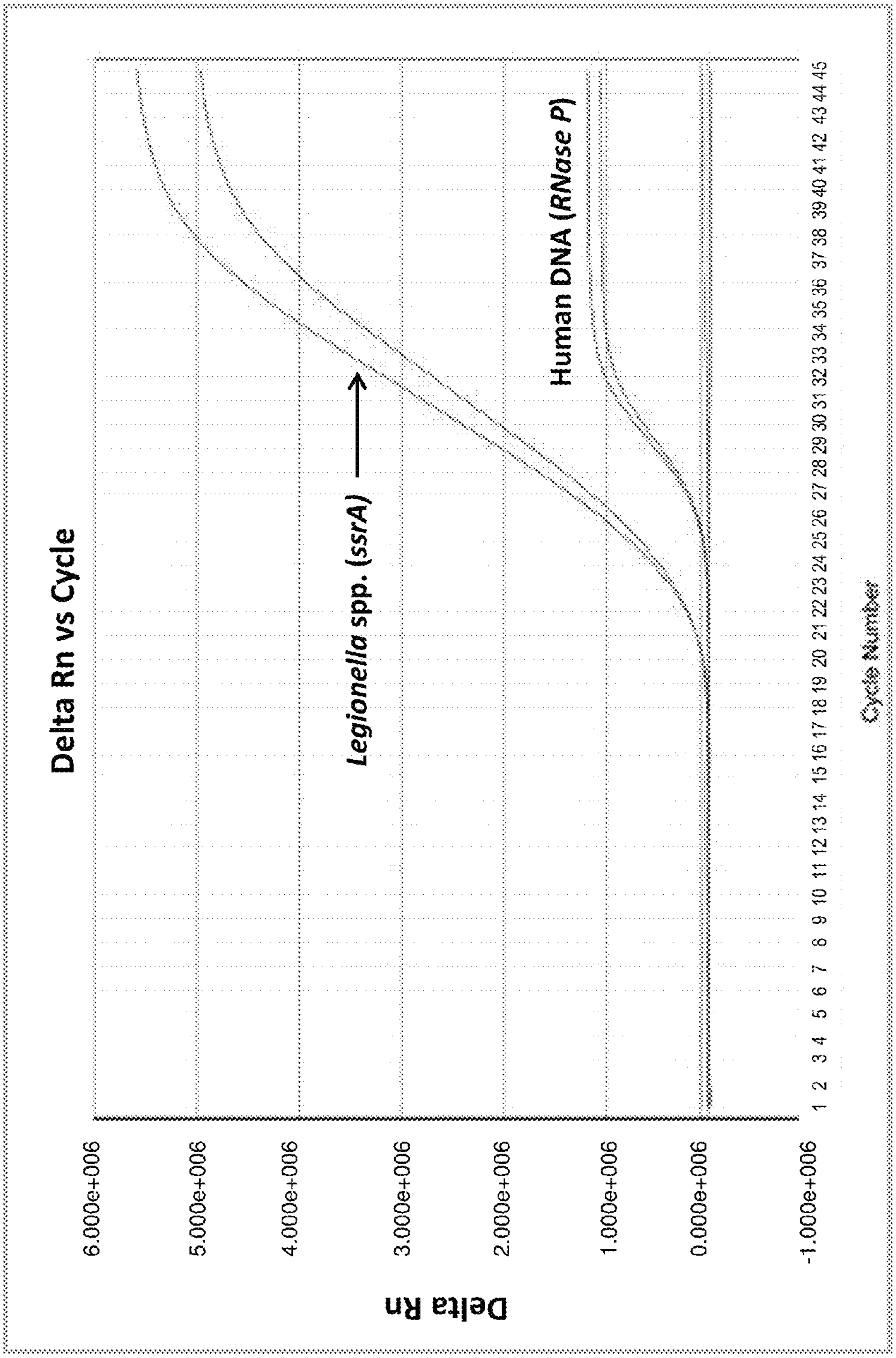
FIG. 1A is a graph showing results from multiplex real-time PCR in a sample containing *L. anisa* DNA and human DNA.

Any nucleic acid and amino acid sequences listed herein or in the accompanying sequence listing are shown using standard letter abbreviations for nucleotide bases, and three letter code for amino acids, as defined in 37 C.F.R. §1.822. In at least some cases, only one strand of each nucleic acid sequence is shown, but the complementary strand is understood as included by any reference to the displayed strand.

The Sequence Listing is submitted as an ASCII text file in the form of the file named Sequence_Listing.txt, which was created on May 14, 2013, and is 14,235 bytes, which is incorporated by reference herein.

SEQ ID NO: 1 is an exemplary *Legionella pneumophila* macrophage infectivity potentiator (mip) gene nucleic acid sequence.

SEQ ID NO: 2 is an exemplary *Legionella* ssrA gene nucleic acid sequence.

SEQ ID NO: 3 is an exemplary *Legionella pneumophila* serogroup 1 wzm gene nucleic acid sequence.

SEQ ID NOs: 4-6 are exemplary *Legionella* spp. ssrA primer and probe nucleic acid sequences.

SEQ ID NOs: 7-9 are exemplary *Legionella pneumophila* mip primer and probe nucleic acid sequences.

SEQ ID NOs: 10-12 are exemplary *Legionella pneumophila* serogroup 1 wzm primer and probe nucleic acid sequences.

SEQ ID NO: 13 is an exemplary *Legionella bozemanii* gyrB nucleic acid sequence.

SEQ ID NO: 14 is an exemplary *Legionella dumoffii* legS2 nucleic acid sequence.

SEQ ID NO: 15 is an exemplary *Legionella feeleii* figA nucleic acid sequence.

SEQ ID NO: 16 is an exemplary *Legionella longbeachae* ligB nucleic acid sequence.

SEQ ID NO: 17 is an exemplary *Legionella micdadei* migB nucleic acid sequence.

SEQ ID NOs: 18-20, 33, and 35 are exemplary *Legionella bozemanii* gyrB primer and probe nucleic acid sequences.

SEQ ID NOs: 21-23 are exemplary *Legionella dumoffii* legS2 primer and probe nucleic acid sequences.

SEQ ID NOs: 24-26, 34, and 36 are exemplary *Legionella feeleii* figA primer and probe nucleic acid sequences.

SEQ ID NOs: 27-29 are exemplary *Legionella longbeachae* ligB primer and probe nucleic acid sequences.

SEQ ID NOs: 30-32 are exemplary *Legionella micdadei* migB primer and probe nucleic acid sequences.

DETAILED DESCRIPTION

Although the majority of cases of Legionnaires' disease are caused by *Legionella pneumophila*, an increasing number of other *Legionella* species have been associated with human disease. Currently, culture remains the standard for identifying Legionellae in both clinical and environmental samples. Although culture has good specificity, it is time-consuming and impractical for timely results. Disclosed herein is are real-time PCR assays, such as single-tube multiplex PCR assays, that allow for the rapid detection of clinically-relevant *Legionella* species in clinical and environmental samples. In some embodiments, the disclosed methods are capable of simultaneously detecting and discriminating *Legionella* spp., *Legionella pneumophila*, and *Legionella pneumophila* serogroup 1 in both clinical samples and water samples with high sensitivity and specificity. In additional embodiments, the disclosed methods are capable of simultaneously detecting and discriminating non-pneumophila *Legionella* species *L. bozemanii, L. dumoffii, L. feeleii, L. longbeachae, L. micdadei, L. sainthelensis, L. anisa, L. parisiensis*, and *L. tucsonensis* in clinical and environmental samples with high sensitivity and specificity. In some embodiments, the disclosed assays can be performed concurrently or sequentially in order to identify presence of *Legionella* spp. and/or particular *Legionella* species or strains in a sample. The assays can be used to complement bacteriological culture and antigen detection, allowing rapid and specific Legionellae diagnosis, especially during outbreak investigations. Furthermore, the disclosed methods may be capable of detecting nucleic acid from non-culturable Legionellae, or Legionellae present within their protozoan hosts, which otherwise would go undetected by culture methods.

I. Abbreviations

MGBNFQ minor groove binder/non-fluorescent quencher
mip macrophage infectivity potentiator
PCR polymerase chain reaction
Sg serogroup

II. Terms

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

Unless otherwise explained, all technical and scientific terms used herein have the same meaning as commonly understood by one of ordinary skill in the art to which this disclosure pertains. The singular terms "a," "an," and "the" include plural referents unless context clearly indicates otherwise. As used herein, "comprises" means "includes." Thus, "comprising A or B," means "including A, B, or A and B," without excluding additional elements. It is further to be understood that all base sizes or amino acid sizes, and all molecular weight or molecular mass values, given for nucleic acids or polypeptides are approximate, and are provided for description. All publications, patent applications, patents, and other references mentioned herein are incorporated by reference in their entirety for all purposes.

Although methods and materials similar or equivalent to those described herein can be used in the practice or testing of the present disclosure, suitable methods and materials are described below. In case of conflict, the present specification, including explanations of terms, will control. In addition, the materials, methods, and examples are illustrative only and not intended to be limiting.

In order to facilitate review of the various embodiments of the disclosure, the following explanations of specific terms are provided:

Amplification: To increase the number of copies of a nucleic acid molecule. The resulting amplification products are called "amplicons." Amplification of a nucleic acid molecule (such as a DNA or RNA molecule) refers to use of a technique that increases the number of copies of a nucleic acid molecule in a sample. An example of amplification is the polymerase chain reaction (PCR), in which a sample is contacted with a pair of oligonucleotide primers under conditions that allow for the hybridization of the primers to a nucleic acid template in the sample. The primers are extended under suitable conditions, dissociated from the template, re-annealed, extended, and dissociated to amplify the number of copies of the nucleic acid. This cycle can be repeated. The product of amplification can be characterized by such techniques as electrophoresis, restriction endonuclease cleavage patterns, oligonucleotide hybridization or ligation, and/or nucleic acid sequencing.

Other examples of in vitro amplification techniques include real-time PCR; quantitative real-time PCR; reverse transcriptase PCR(RT-PCR); real-time reverse transcriptase PCR (rt RT-PCR); nested PCR; strand displacement amplification (see U.S. Pat. No. 5,744,311); transcription-free isothermal amplification (see U.S. Pat. No. 6,033,881); repair chain reaction amplification (see WO 90/01069); ligase chain reaction amplification (see European patent publication EP-A-320 308); gap filling ligase chain reaction amplification (see U.S. Pat. No. 5,427,930); coupled ligase detection and PCR (see U.S. Pat. No. 6,027,889); and NASBA™ RNA transcription-free amplification (see U.S. Pat. No. 6,025,134), amongst others.

Detect: To determine if an agent (such as a signal, particular nucleotide, amino acid, nucleic acid molecule, and/or organism) is present or absent, for example *Legionella* spp., *Legionella pneumophila, Legionella pneumophila* serogroup 1, *Legionella bozemanii, Legionella dumoffii, Legionella feeleii, Legionella longbeachae*, or *Legionella micdadei*. In some examples, this can further include quantification. For example, use of the disclosed probes in particular examples permits detection of a fluorophore, for example, detection of a signal from a fluorophore, which can be used to determine if a nucleic acid corresponding to a *Legionella* spp., *Legionella pneumophila, Legionella pneumophila* serogroup 1, *Legionella bozemanii, Legionella dumoffii, Legionella feeleii, Legionella longbeachae*, or *Legionella micdadei* nucleic acid is present. The detection of a nucleic acid molecule of the particular bacteria indicates the presence of the bacteria in the sample.

Discriminate: To distinguish or detect differences between two or more things, for example to distinguish or detect the presence of a particular bacteria (as opposed to others) in a sample. In some examples, the disclosed methods distinguish or detect whether *Legionella* spp., *Legionella pneumophila*, and/or *Legionella pneumophila* serotype 1 are present in a sample. In other examples, the disclosed methods distinguish or detect whether *Legionella bozemanii, Legionella dumoffii, Legionella feeleii, Legionella longbeachae*, and/or *Legionella micdadei* is present in a sample DNA gyrase, subunit B (gyrB): The gyrB gene is a type II topoisomerase. GenBank Accession Nos. HQ717438 and JF720461 provide exemplary *Legionella bozemanii* (also known as *Fluoribacter bozemanae*) gyrB nucleic acid sequences, each of which are incorporated by reference herein as present in GenBank on Mar. 1, 2013. An exemplary *Legionella bozemanii* nucleotide sequence of gyrB is set forth as SEQ ID NO: 13.

figA: A member of the fir (functional homologues of icmR) gene family; part of the dot/icm secretion system of *Legionella*. GenBank Accession No. AY753535 provides an exemplary *Legionella feeleii* figA nucleic acid sequence, which is incorporated herein by reference as present in GenBank on Mar. 1, 2013. An exemplary *Legionella feeleii* nucleotide sequence of figA is set forth as SEQ ID NO: 15.

Fluorophore: A chemical compound, which when excited by exposure to a particular stimulus, such as a defined wavelength of light, emits light (fluoresces), for example at a different wavelength (such as a longer wavelength of light).

Fluorophores are part of the larger class of luminescent compounds. Luminescent compounds include chemiluminescent molecules, which do not require a particular wavelength of light to luminesce, but rather use a chemical source of energy. Therefore, the use of chemiluminescent molecules (such as aequorin) eliminates the need for an external source of electromagnetic radiation, such as a laser.

Examples of particular fluorophores that can be used in the probes and primers disclosed herein are known to those of ordinary skill in the art and include those provided in U.S. Pat. No. 5,866,366 to Nazarenko et al., such as 4-acetamido-4'-isothiocyanatostilbene-2,2' disulfonic acid; acridine and derivatives such as acridine and acridine isothiocyanate, 5-(2'-aminoethyl)aminonaphthalene-1-sulfonic acid (EDANS), 4-amino-N-[3-vinylsulfonyl)phenyl]naphthalimide-3,5 disulfonate (Lucifer Yellow VS), N-(4-anilino-1-naphthyl)maleimide, anthranilamide; Brilliant Yellow; coumarin and derivatives such as coumarin, 7-amino-4-methylcoumarin (AMC, Coumarin 120), 7-amino-4-trifluoromethylcouluarin (Coumaran 151); cyanosine; 4',6-diaminidino-2-phenylindole (DAPI); 5',5"-dibromopyrogallol-sulfonephthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino] naphthalene-1-sulfonyl chloride (DNS, dansyl chloride); 4-dimethylaminophenylazophenyl-4'-isothiocyanate (DABITC); eosin and derivatives such as eosin and eosin isothiocyanate; erythrosin and derivatives such as erythrosin B and erythrosin isothiocyanate; ethidium; fluorescein and derivatives such as 5-carboxyfluorescein (FAM), 5-(4,6-dichlorotriazin-2-yl)aminofluorescein (DTAF), 2'7'-dimethoxy-4'5'-dichloro-6-carboxyfluorescein (JOE), fluorescein, fluorescein isothiocyanate (FITC), QFITC (XRITC), 6-carboxyfluorescein (HEX), and TET (tetramethyl fluorescein); fluorescamine; IR144; IR1446; Malachite Green isothiocyanate; 4-methylumbelliferone; ortho-cresolphthalein; nitrotyrosine; pararosaniline; Phenol Red; B-phycoerythrin; o-phthaldialdehyde; pyrene and derivatives such as pyrene, pyrene butyrate, and succinimidyl 1-pyrene butyrate; Reactive Red 4 (CIBACRON™ Brilliant Red 3B-A); rhodamine and derivatives such as 6-carboxy-X-rhodamine (ROX), 6-carboxyrhodamine (R6G), lissamine rhodamine B sulfonyl chloride, rhodamine (Rhod), rhodamine B, rhodamine 123, rhodamine X isothiocyanate, N,N,N',N'-tetramethyl-6-carboxyrhodamine (TAMRA), tetramethyl rhodamine, and tetramethyl rhodamine isothiocyanate (TRITC); sulforhodamine B; sulforhodamine 101 and sulfonyl chloride derivative of sulforhodamine 101 (Texas Red or Texas Red 615); riboflavin; rosolic acid and terbium chelate derivatives; LightCycler Red 640; Cy5.5; and Cy56-carboxyfluorescein; boron dipyrromethene difluoride (BODIPY); acridine; stilbene; Cy3; Cy5, VIC® (Applied Biosystems); LC Red 640; LC Red 705; and Yakima yellow amongst others. Additional examples of fluorophores include Quasar® 670, Quasar® 570, Quasar® 705, CAL Fluor® Red 590, CAL Fluor® Red 610, CAL Fluor® 615, CAL Fluor® Red 635, CAL Fluor® Green 520, CAL Fluor® Gold 540, and CAL Fluor® Orange 560 (Biosearch Technologies, Novato, Calif.).

Other suitable fluorophores include those known to those of ordinary skill in the art, for example those available from Molecular Probes/Life Technologies (Carlsbad, Calif.). In particular examples, a fluorophore is used as a donor fluorophore or as an acceptor fluorophore.

"Acceptor fluorophores" are fluorophores which absorb energy from a donor fluorophore, for example in the range of about 400 to 900 nm (such as in the range of about 500 to 800 nm). Acceptor fluorophores generally absorb light at a wavelength which is usually at least 10 nm higher (such as at least 20 nm higher) than the maximum absorbance wavelength of the donor fluorophore, and have a fluorescence emission maximum at a wavelength ranging from about 400 to 900 nm. Acceptor fluorophores have an excitation spectrum that overlaps with the emission of the donor fluorophore, such that energy emitted by the donor can excite the acceptor. Ideally, an acceptor fluorophore is capable of being attached to a nucleic acid molecule.

In a particular example, an acceptor fluorophore is a dark quencher, such as Dabcyl, QSY7 (Molecular Probes), QSY33 (Molecular Probes), BLACK HOLE QUENCHERS™ (Biosearch Technologies; such as BHQ0, BHQ1, BHQ2, and BHQ3), ECLIPSE™ Dark Quencher (Epoch Biosciences), or IOWA BLACK™ (Integrated DNA Technologies). In other examples, an acceptor fluorophore is a minor groove binder/non-fluorescent quencher (MGBNFQ). A quencher can reduce or quench the emission of a donor fluorophore. In such an example, instead of detecting an increase in emission signal from the acceptor fluorophore when in sufficient proximity to the donor fluorophore (or detecting a decrease in emission signal from the acceptor fluorophore when a significant distance from the donor fluorophore), an increase in the emission signal from the donor fluorophore can be detected when the quencher is a significant distance from the donor fluorophore (or a decrease in emission signal from the donor fluorophore when in sufficient proximity to the quencher acceptor fluorophore).

"Donor Fluorophores" are fluorophores or luminescent molecules capable of transferring energy to an acceptor fluorophore, thereby generating a detectable fluorescent signal from the acceptor. Donor fluorophores are generally compounds that absorb in the range of about 300 to 900 nm, for example about 350 to 800 nm. Donor fluorophores have a strong molar absorbance coefficient at the desired excitation wavelength, for example greater than about $10^3$ $M^{-1}$ $cm^{-1}$.

Hybridization: The ability of complementary single-stranded DNA or RNA to form a duplex molecule (also referred to as a hybridization complex). Nucleic acid hybridization techniques can be used to form hybridization complexes between a probe or primer and a nucleic acid, such as a *Legionella* nucleic acid. For example, a probe or primer (such as any one of SEQ ID NOs: 4-12 or 18-32) having some homology to a disclosed *Legionella* nucleic acid molecule will form a hybridization complex with a complementary nucleic acid molecule (such as any one of SEQ ID NOs: 1-3 or 13-17).

Hybridization conditions resulting in particular degrees of stringency will vary depending upon the nature of the hybridization method and the composition and length of the hybridizing nucleic acid sequences. Generally, the temperature of hybridization and the ionic strength (such as the $Na^+$ concentration) of the hybridization buffer will determine the stringency of hybridization. Calculations regarding hybridization conditions for attaining particular degrees of stringency are discussed in Sambrook et al., (1989) *Molecular Cloning*, second edition, Cold Spring Harbor Laboratory, Plainview, N.Y. (chapters 9 and 11). The following is an exemplary set of hybridization conditions and is not limiting:

Very High Stringency (Detects Sequences that Share at Least 90% Identity)

Hybridization: 5×SSC at 65° C. for 16 hours

Wash twice: 2×SSC at room temperature (RT) for 15 minutes each

Wash twice: 0.5×SSC at 65° C. for 20 minutes each

High Stringency (Detects Sequences that Share at Least 80% Identity)

Hybridization: 5×-6×SSC at 65° C.–70° C. for 16-20 hours

Wash twice: 2×SSC at RT for 5-20 minutes each

Wash twice: 1×SSC at 55° C.-70° C. for 30 minutes each

Low Stringency (Detects Sequences that Share at Least 50% Identity)

Hybridization: 6×SSC at RT to 55° C. for 16-20 hours

Wash at least twice: 2×-3×SSC at RT to 55° C. for 20-30 minutes each.

The probes and primers disclosed herein can hybridize to nucleic acid molecules under low stringency, high stringency, or very high stringency conditions.

Label (Detectable label): An agent capable of detection, for example by spectrophotometry, flow cytometry, or microscopy. For example, a label can be attached to a nucleotide, thereby permitting detection of the nucleotide, such as detection of the nucleic acid molecule of which the nucleotide is a part, such as a probe and/or primer. Examples of labels include, but are not limited to, radioactive isotopes, enzyme substrates, co-factors, ligands, chemiluminescent agents, fluorophores, haptens, enzymes, and combinations thereof. Methods for labeling and guidance in the choice of labels appropriate for various purposes are discussed for example in Sambrook et al. (*Molecular Cloning: A Laboratory Manual*, Cold Spring Harbor, N.Y., 1989) and Ausubel et al. (In *Current Protocols in Molecular Biology*, John Wiley & Sons, New York, 1998).

*Legionella*: A genus of gram-negative bacteria that cause Legionellosis, including pneumonia. *L. pneumophila* Sg1 is most common, causing about 70% of cases of Legionellosis. *L. pneumophila* Sg2, Sg4, and Sg6, as well as *L. bozemanii, L. longbeachae*, and *L. micdadei* also have been reported as causing disease. Additional *Legionella* species include *L. dumoffii, L. feeleii, L. sainthelensis, L. anisa, L. parisiensis*, and *L. tucsonensis*. Additional *Legionella* species include those listed in Fields et al., *Clin. Microbiol. Rev.* 15:506-526, 2002. Nucleic acid and protein sequences for *Legionella* spp. are publicly available. For example, GenBank Accession Nos. NC_009494, NC_006369, NC_006368, NC_002942, NZ_CM001371, and NC_013681 provide exemplary *Legionella* genome sequences all of which are incorporated by reference herein as present in Genbank on Mar. 1, 2013.

ligB: A member of the fir (functional homologues of icmR) gene family; part of the dot/icm secretion system of *Legionella*. GenBank Accession Nos. NC_013681 (3269819-3270085; reverse complement) and AY512558 provide exemplary *Legionella longbeachae* ligB nucleic acid sequences, which are incorporated herein by reference as present in GenBank on Mar. 1, 2013. An exemplary *Legionella longbeachae* nucleotide sequence of ligB is set forth as SEQ ID NO: 16.

Macrophage infectivity potentiator (mip): A major virulence factor expressed by *Legionella pneumophila*. Mip is an enzyme with peptidyl-prolyl-cis/trans isomerase activity. GenBank Accession Nos. CP00312 (881105-881812), CP000675 (975812-976513), JN697587, and AF095225 provide exemplary *Legionella* mip nucleic acid sequences, each of which are incorporated by reference herein as present in GenBank on Jun. 11, 2012. An exemplary *Legionella pneumophila* nucleotide sequence of mip is set forth as SEQ ID NO: 1.

migB: A member of the fir (functional homologues of icmR) gene family; part of the dot/icm secretion system of *Legionella*. GenBank Accession No. AY512559 provides an exemplary *Legionella micdadei* (also known as *Tatlockia micdadei*) migB nucleic acid sequence, which is incorporated herein by reference as present in GenBank on Mar. 1, 2013. An exemplary *Legionella micdadei* nucleotide sequence of migB is set forth as SEQ ID NO: 17.

Multiplex PCR: Amplification of multiple nucleic acid species in a single PCR reaction, such as a single real-time PCR reaction. By multiplexing, target nucleic acids (including an endogenous control, in some examples) can be amplified in single tube. In some examples, multiplex PCR permits the simultaneous detection of the amplification products of *Legionella* nucleic acids using the disclosed probes or even another nucleic acid, such as a control nucleic acid, for example a human RNase P nucleic acid.

Primer: Short nucleic acid molecules, for instance DNA oligonucleotides 10-100 nucleotides in length, such as about 10, 15, 20, 25, 30, 40, 45, or 50 nucleotides or more in length. Primers can be annealed to a complementary target DNA strand by nucleic acid hybridization to form a hybrid between the primer and the target DNA strand. A primer can be extended along the target nucleic acid molecule by a polymerase enzyme. Therefore, primers can be used to amplify a target nucleic acid molecule, wherein the sequence of the primer is specific for the target nucleic acid molecule, for example so that the primer will hybridize to the target nucleic acid molecule under very high stringency hybridization conditions.

Primer pairs can be used for amplification of a nucleic acid sequence, for example, by PCR, real-time PCR, or other nucleic-acid amplification methods known in the art. An "upstream" or "forward" primer is a primer 5' to a reference point on a nucleic acid sequence. A "downstream" or "reverse" primer is a primer 3' to a reference point on a nucleic acid sequence.

In particular examples, a primer is at least 10 nucleotides in length, such as at least 10 contiguous nucleotides complementary to a target nucleic acid molecule. Particular lengths of primers that can be used to practice the methods of the present disclosure include primers having at least 10, such as at least 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or more contiguous nucleotides complementary to the target nucleic acid molecule to be amplified, such as a primer of 10-60 nucleotides, 15-50 nucleotides, 20-40 nucleotides, 25-50, nucleotides, or 10-40 nucleotides.

Methods for preparing and using nucleic acid primers are described, for example, in Sambrook et al. (In *Molecular Cloning: A Laboratory Manual*, CSHL, New York, 1989), Ausubel et al. (ed.) (In *Current Protocols in Molecular Biology*, John Wiley & Sons, New York, 1998), and Innis et al. (*PCR Protocols, A Guide to Methods and Applications*, Academic Press, Inc., San Diego, Calif., 1990). PCR primer pairs can be derived from a known sequence, for example, by using computer programs intended for that purpose such as Primer (Version 0.5, 1991, Whitehead Institute for Biomedical Research, Cambridge, Mass.). One of ordinary skill in the art will appreciate that the specificity of a particular primer increases with its length. Thus, in order to obtain greater specificity, primers can be selected that include at least 10, at least 15, at least 20, at least 25, at least 30, at least 35, at least 40, at least 45, at least 50 or more consecutive nucleotides of a target sequence.

Probe: A short sequence of nucleotides, such as at least 8, at least 10, at least 15, at least 20, at least 25, or at least 30 nucleotides in length, used to detect the presence of a complementary sequence by molecular hybridization. In particular examples, probes include a label that permits detection of probe:target sequence hybridization complexes. Typical labels include radioactive isotopes, enzyme substrates, cofactors, ligands, chemiluminescent or fluorescent agents, haptens, and enzymes. Methods for labeling and guidance in the choice of labels appropriate for various purposes are discussed, for example, in Sambrook et al., *Molecular Cloning: A Laboratory Manual*, Cold Spring Harbor Laboratory Press (1989) and Ausubel et al., *Current Protocols in Molecular Biology*, Greene Publishing Associates and Wiley-Intersciences (1987).

In a particular example, a probe includes at least one fluorophore, such as an acceptor fluorophore or donor fluorophore. For example, a fluorophore can be attached at the 5'- or 3'-end of the probe. In specific examples, the fluorophore is attached to the base at the 5'-end of the probe, the base at its 3'-end, the phosphate group at its 5'-end, or a modified base, such as a T internal to the probe.

Probes are generally at least 10 nucleotides in length, such as at least 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 51, 52, 53, 54, 55, 56, 57, 58, 59, 60, or more contiguous nucleotides complementary to the target nucleic acid molecule, such as 10-60 nucleotides, 30-60 nucleotides, 20-50 nucleotides, 30-50 nucleotides, 20-40 nucleotides, or 10-40 nucleotides.

Real-time PCR: A method for detecting and measuring products generated during each cycle of a PCR, which are proportionate to the amount of template nucleic acid prior to the start of PCR. The information obtained, such as an amplification curve, can be used to determine the presence of a target nucleic acid (such as a *Legionella* nucleic acid) and/or quantitate the initial amounts of a target nucleic acid sequence. Exemplary procedures for real-time PCR can be found in "Quantitation of DNA/RNA Using Real-Time PCR Detection" published by Perkin Elmer Applied Biosystems (1999); *PCR Protocols* (Academic Press, New York, 1989); and *A-Z of Quantitative PCR*, Bustin (ed.), International University Line, La Jolla, Calif., 2004.

In some examples, the amount of amplified target nucleic acid is detected using a labeled probe, such as a probe labeled with a fluorophore, for example a TAQMAN® probe. In this example, the increase in fluorescence emission is measured in real-time, during the course of the real-time PCR. This increase in fluorescence emission is directly related to the increase in target nucleic acid amplification. In some examples, the change in fluorescence (dRn) is calculated using the equation $dRn=Rn^{+}-Rn^{-}$, with $Rn^{+}$ being the fluorescence emission of the product at each time point and $Rn^{-}$ being the fluorescence emission of the baseline. The dRn values are plotted against cycle number, resulting in amplification plots for each sample. The threshold value (CO is the PCR cycle number at which the fluorescence emission (dRn) exceeds a chosen threshold, which is typically 10 times the standard deviation of the baseline (this threshold level can, however, be changed if desired).

The threshold cycle is when the system begins to detect the increase in the signal associated with an exponential growth of PCR product during the log-linear phase. This phase provides information about the reaction. The slope of the log-linear phase is a reflection of the amplification efficiency. The efficiency of the reaction can be calculated by the following equation: $E=10^{(-1/slope)}$. The efficiency of the PCR should be 90-100%, meaning doubling of the amplicon at each cycle. This corresponds to a slope of −3.1 to −3.6 in the $C_t$ vs. log-template amount standard curve. In order to obtain accurate and reproducible results, reactions should have efficiency as close to 100% as possible (meaning a two-fold increase of amplicon at each cycle).

Sample: As used herein, a sample (for example a biological sample) includes all clinical samples useful for detecting *Legionella* in subjects, including, but not limited to, cells, tissues, and bodily fluids, such as: blood; derivatives and fractions of blood, such as serum; extracted galls; biopsied or surgically removed tissue, including tissues that are, for example, unfixed, frozen, fixed in formalin, and/or embedded in paraffin; autopsy material; tears; milk; skin scrapes; surface washings; urine; sputum; cerebrospinal fluid; prostate fluid; pus; bone marrow aspirates; middle ear fluids; bronchoalveolar lavage; tracheal aspirates; nasopharyngeal aspirates or swabs; oropharyngeal aspirates or swabs; or saliva. A sample may also include environmental samples, for example, food, water (such as water from cooling towers, central air conditioning systems, swimming pools, domestic water systems, fountains, or freshwater creeks or ponds), or other materials that may contain or be contaminated with *Legionella*.

Sensitivity and specificity: Statistical measurements of the performance of a binary classification test. Sensitivity measures the proportion of actual positives which are correctly identified (e.g., the percentage of samples that are identified as including nucleic acid from a particular organism). Specificity measures the proportion of negatives which are correctly identified (e.g., the percentage of samples that are identified as not including nucleic acid from a particular organism).

Sequence identity/similarity: The identity/similarity between two or more nucleic acid sequences, or two or more amino acid sequences, is expressed in terms of the identity or similarity between the sequences. Sequence identity can be measured in terms of percentage identity; the higher the percentage, the more identical the sequences are. Homologs or orthologs of nucleic acid or amino acid sequences possess a relatively high degree of sequence identity/similarity when aligned using standard methods.

Methods of alignment of sequences for comparison are well known in the art. Various programs and alignment algorithms are described in: Smith & Waterman, *Adv. Appl. Math.* 2:482, 1981; Needleman & Wunsch, *J. Mol. Biol.* 48:443, 1970; Pearson & Lipman, *Proc. Natl. Acad. Sci. USA* 85:2444, 1988; Higgins & Sharp, *Gene,* 73:237-44, 1988; Higgins & Sharp, *CABIOS* 5:151-3, 1989; Corpet et al., *Nuc. Acids Res.* 16:10881-90, 1988; Huang et al. *Computer Appls. in the Biosciences* 8, 155-65, 1992; and Pearson et al., *Meth. Mol. Bio.* 24:307-31, 1994. Altschul et al., *J. Mol. Biol.* 215:403-10, 1990, presents a detailed consideration of sequence alignment methods and homology calculations.

The NCBI Basic Local Alignment Search Tool (BLAST) (Altschul et al., *J. Mol. Biol.* 215:403-10, 1990) is available from several sources, including the National Center for Biological Information (NCBI, National Library of Medicine, Building 38A, Room 8N805, Bethesda, Md. 20894) and on the Internet, for use in connection with the sequence analysis programs blastp, blastn, blastx, tblastn, and tblastx. Blastn is used to compare nucleic acid sequences, while blastp is used to compare amino acid sequences. Additional information can be found at the NCBI web site.

Once aligned, the number of matches is determined by counting the number of positions where an identical nucleotide or amino acid residue is present in both sequences. The percent sequence identity is determined by dividing the number of matches either by the length of the sequence set forth in the identified sequence, or by an articulated length (such as 100 consecutive nucleotides or amino acid residues from a sequence set forth in an identified sequence), followed by multiplying the resulting value by 100.

One indication that two nucleic acid molecules are closely related is that the two molecules hybridize to each other under stringent conditions. Stringent conditions are sequence-dependent and are different under different environmental parameters. The nucleic acid probes and primers disclosed herein are not limited to the exact sequences shown, as those of ordinary skill in the art will appreciate that changes can be made to a sequence, and not substantially affect the ability of the probe or primer to function as desired. For example, sequences having at least 80%, at least 85%, at least 90%, at least 91%, at least 92%, at least 93%, at least 94%, at least 95%, at least 96%, at least 97%, at least 98%, or at least 99%, such as 100% sequence identity to any of SEQ ID NOs: 4-12 and 18-32 are provided herein. One of ordinary skill in the art will appreciate that these sequence identity ranges are provided for guidance only; it is possible that probes and primer can be used that fall outside these ranges.

Signal: A detectable change or impulse in a physical property that provides information. In the context of the disclosed methods, examples include electromagnetic signals such as light, for example light of a particular quantity or wavelength. In certain examples, the signal is the disappearance of a physical event, such as quenching of light.

Sphingosine 1-phosphate lyase (legS2): The legS2 gene is a sphingosine 1-phosphate lyase. GenBank Accession No. EU107519 provides an exemplary *Legionella dumoffii* (also known as *Fluoribacter dumoffii*) legS2 nucleic acid sequence, which is incorporated by reference herein as present in GenBank on Mar. 1, 2013. An exemplary *Legionella dumoffii* nucleotide sequence of legS2 is set forth as SEQ ID NO: 14.

ssrA: The *Legionella* ssrA gene (also known as 10Sa RNA or tmRNA) is an RNA with tRNA-like and mRNA-like properties that mediates tagging for degradation of a protein product of a ribosome that reaches the end of an mRNA without encountering a stop codon (Williams and Bartel, *RNA* 2:1306-1310, 1996). GenBank Accession Nos. U68079, AE017354 (172764-173400), CP628337 (175142-175503), CR628336 (182399-182760), CP000675 (181371-181732), and FN650140 (complement, 3822176-3821816) provide exemplary *Legionella* ssrA nucleic acid sequences, each of which are incorporated by reference herein as present in GenBank on Jun. 11, 2012. An exemplary *Legionella pneumophila* nucleotide sequence of ssrA is set forth as SEQ ID NO: 2.

Subject: A living multi-cellular vertebrate organism, a category that includes human and non-human mammals.

Target nucleic acid molecule: A nucleic acid molecule whose detection, quantitation, qualitative detection, or a combination thereof, is intended. The nucleic acid molecule need not be in a purified form. Various other nucleic acid molecules can also be present with the target nucleic acid molecule. For example, the target nucleic acid molecule can be a specific nucleic acid molecule (which can include RNA or DNA), the amplification of which is intended. Purification or isolation of the target nucleic acid molecule, if needed, can be conducted by methods known to those of ordinary skill in the art, such as by using a commercially available purification kit.

wzm: The *Legionella* wzm gene is a lipopolysaccharide O-antigen ABC transporter. GenBank Accession Nos. AE017354 (845134-845985), NC_009494 (954539-955390), NC_006368 (937793-938644), and NC_006369 (920141-920992) provide exemplary *Legionella* wzm nucleic acid sequences, each of which are incorporated by reference herein as present in GenBank on Jun. 11, 2012. An exemplary *Legionella pneumophila* nucleotide sequence of wzm is set forth as SEQ ID NO: 3.

III. Methods for Detection or Discrimination of *Legionella*

Methods for detecting the presence of *Legionella* and/or discriminating presence of *Legionella* spp., *Legionella pneumophila, Legionella pneumophila* serogroup 1, *Legionella bozemanii, Legionella dumoffii, Legionella feeleii, Legionella longbeachae, Legionella micdadei, Legionella sainthelensis, Legionella anisa, Legionella parisiensis*, and/or *Legionella tucsonensis* in a sample are disclosed, for example, utilizing the primers and probes disclosed herein. In some embodiments, the disclosed methods include detecting and/or discriminating presence of *Legionella* spp., *Legionella pneumophila*, and/or *Legionella pneumophila* serogroup 1 in a sample. In other embodiments, the disclosed methods include detecting and/or discriminating presence of *Legionella bozemanii, Legionella dumoffii, Legionella feeleii, Legionella longbeachae, Legionella micdadei, Legionella sainthelensis, Legionella anisa, Legionella parisiensis*, and/or *Legionella tucsonensis* in a sample. In still further embodiments, the disclosed methods include detecting presence of *Legionella* spp. in a sample and further detecting or discriminating presence of *Legionella bozemanii, Legionella dumoffii, Legionella feeleii, Legionella longbeachae, Legionella micdadei, Legionella sainthelensis, Legionella anisa, Legionella parisiensis*, and/or *Legionella tucsonensis* in the sample.

The methods described herein may be used for any purpose for which detection of *Legionella* is desirable, including diagnostic and prognostic applications, such as in laboratory and clinical settings. Appropriate samples include any conventional environmental or biological samples, including clinical samples obtained from a human or veterinary subject. Suitable samples include all biological samples useful for detection of bacterial infection in subjects, including, but not limited to, cells, tissues (for example, lung, liver, and kidney), autopsy samples, bone marrow aspirates, bodily fluids (for example, blood, serum, urine, cerebrospinal fluid, middle ear fluids, bronchoalveolar lavage, tracheal aspirates, sputum, nasopharyngeal aspirates, oropharyngeal aspirates, or saliva), eye swabs, cervical swabs, vaginal swabs, rectal swabs, stool, and stool suspensions. Suitable samples also include all environmental samples useful for detection, monitoring, or surveillance of bacterial contamination, including, but not limited to, food, water (such as water from cooling towers, central air conditioning systems, swimming pools, domestic water systems, fountains, or freshwater creeks or ponds), or other materials that may contain or be contaminated with *Legionella*.

In some embodiments, the nucleic acids detected using the methods provided herein include nucleic acid molecules from *Legionella*. In some examples, *Legionella* includes, but is not limited to, *L. pneumophila* (such as *L. pneumophila* subtypes Sg1, Sg2, Sg3, Sg4, Sg5, Sg6, Sg7, Sg8, Sg9, Sg10, Sg11, Sg12, Sg13, or Sg14), *L. bozemanii, L. longbeachae, L. micdadei, L. birminghamensis, L. dumoffii, L. feeleii, L. hackliae, L. maceachernii*, and *L. wadsworthii*. Additional *Legionella* species and serogroups include those shown in Table 2 (below) and in Fields et al., *Clin. Microbiol. Rev.* 15:506-526, 2002, incorporated herein by reference. Bacterial strains may be obtained from patient or environmental samples or bacterial collections, for example, the American Type Culture Collection (Manassas, Va.).

One of ordinary skill in the art will know suitable methods for extracting nucleic acids such as RNA and/or DNA from a sample; such methods will depend upon, for example, the type of sample in which the *Legionella* nucleic acid is found. Nucleic acids can be extracted using standard methods. For instance, rapid nucleic acid preparation can be performed using a commercially available kit (such as kits and/or instruments from Qiagen (such as DNEasy® or RNEasy® kits), Roche Applied Science (such as MagNA Pure kits and instruments), Thermo Scientific (KingFisher mL), bioMérieux (Nuclisens® NASBA Diagnostics), or Epicentre (Masterpure™ kits)). In other examples, the nucleic acids may be extracted using guanidinium isothiocyanate, such as single-step isolation by acid guanidinium isothiocyanate-phenol-chloroform extraction (Chomczynski et al. *Anal. Biochem.* 162:156-159, 1987). The sample can be used directly or can be processed, such as by adding solvents, preservatives, buffers, or other compounds or substances.

Detecting presence of at least one *Legionella* nucleic acid in a sample involves contacting the sample with at least one of the probes (such as 1, 2, 3, 4, 5, 6, 7, or 8 probes) disclosed herein that is capable of hybridizing to a *Legionella* spp. nucleic acid (such as a *Legionella* spp. ssrA nucleic acid), a *Legionella pneumophila* nucleic acid (such as a *Legionella pneumophila* mip nucleic acid), a *Legionella pneumophila* serogroup 1 nucleic acid (such as a *Legionella pneumophila* serogroup 1 wzm nucleic acid), a *Legionella bozemanii* nucleic acid (such as a *Legionella bozemanii* gyrB nucleic acid), a *Legionella dumoffii* nucleic acid (such as a *Legionella dumoffii* legS2 nucleic acid), a *Legionella feeleii* nucleic acid (such as a *Legionella feeleii* figA nucleic acid), a *Legionella longbeachae* nucleic acid (such as a *Legionella longbeachae* ligB nucleic acid), or a *Legionella micdadei* nucleic acid (such as a *Legionella micdadei* migB nucleic acid) under conditions of high or very high stringency. In particular examples, the probes are detectably labeled (for example, as described in section IV, below). In some examples, the probes are at least 10, 15, 20, 25, 30, 35, or 40 nucleotides in length. In other examples, the probes may be no more than 10, 15, 20, 25, 30, 35, or 40 nucleotides in length.

One of ordinary skill in the art can determine low, high, or very high stringency conditions for hybridization of a primer or probe (such as a probe or primer disclosed herein) to a nucleic acid sequence (for example to one of SEQ ID NOs: 1-3 or 13-17). In some examples, the conditions are for hybridization of a primer or probe to a nucleic acid attached to a solid support (such as the conditions provided above). In other examples, the conditions are for hybridization of a primer or probe to a nucleic acid in solution, such as a PCR reaction mixture. In some non-limiting examples, low stringency conditions include hybridization (such as an annealing step in PCR) at a temperature of about 45-50° C. In other examples, high stringency conditions include hybridization (such as an annealing step in PCR) at a temperature of about 50-60° C. In further examples, very high stringency conditions include hybridization (such as an annealing step in PCR) at a temperature of greater than 60° C. One of ordinary skill in the art can determine appropriate hybridization or annealing conditions (including the degree of hybridization) based on the particular primers or probes and target nucleic acids to be amplified or detected.

In one embodiment, the methods include contacting the sample with a first probe comprising a nucleic acid molecule between 10 and 40 nucleotides in length, wherein the first probe is capable of hybridizing under very high stringency conditions to a *Legionella* ssrA nucleic acid sequence set forth as SEQ ID NO: 2; contacting the sample with a second probe comprising a nucleic acid molecule between 10 and 40 nucleotides in length, wherein the second probe is capable of hybridizing under very high stringency conditions to a *Legionella pneumophila* mip nucleic acid sequence set forth as SEQ ID NO: 1; and contacting the sample with a third probe comprising a nucleic acid molecule between 10 and 40 nucleotides in length, wherein the third probe is capable of hybridizing under very high stringency conditions to a *Legionella pneumophila* serogroup 1 wzm nucleic acid sequence set forth as SEQ ID NO: 3, wherein each of the first, second, and third probes are detectably labeled; and the method further includes detecting hybridization between one or more probe and nucleic acid, wherein detection of hybridization between the first probe and a nucleic acid (such as SEQ ID NO: 2 or a portion thereof) indicates the presence of *Legionella* spp. nucleic acid in the sample, detection of hybridization between the second probe and a nucleic acid (such as SEQ ID NO: 1 or a portion thereof) indicates the presence of *Legionella pneumophila* nucleic acid in the sample, and detection of hybridization between the third probe and a nucleic acid (such as SEQ ID NO: 3 or a portion thereof) indicates the presence of *Legionella pneumophila* serogroup 1 nucleic acid in the sample. In some examples, the sample is contacted with each of the probes in the same reaction, such as a multiplex PCR reaction. In other examples, the sample is contacted with each of the probes in separate reactions.

For example, in some embodiments the disclosed methods include contacting a sample with at least one of the probes (such as one, two, or three probes) disclosed herein such as a nucleic acid probe capable of hybridizing under very high stringency conditions to a *Legionella* spp. ssrA nucleic acid sequence set forth as SEQ ID NO: 2, a *Legionella pneumophila* mip nucleic acid sequence set forth as SEQ ID NO: 1, or a *Legionella pneumophila* serogroup 1 wzm nucleic acid sequence set forth as SEQ ID NO: 3 (for example a nucleic acid sequence at least 90% identical to the nucleotide sequence set forth as one of SEQ ID NO: 6, SEQ ID NO: 9, or SEQ ID NO: 12, such as a nucleic acid sequence consisting essentially of the nucleic acid sequence set forth as one of SEQ ID NO: 6, SEQ ID NO: 9, or SEQ ID NO: 12), and detecting hybridization between a nucleic acid and the respective probe. In particular examples, the probes are detectably labeled (for example, as described in section IV, below). Detection of hybridization between the *Legionella* spp. ssrA probe (for example SEQ ID NO: 6) and a nucleic acid indicates the presence of *Legionella* spp. nucleic acid in the sample, detection of hybridization between the *Legionella pneumophila* mip probe (for example, SEQ ID NO: 9) and a nucleic acid indicates the presence of *Legionella pneumophila* nucleic acid in the sample, and detection of hybridization between the *Legionella pneumophila* serogroup 1 wzm probe (for example SEQ ID NO: 12) and a nucleic acid indicates the presence of *Legionella pneumophila* serogroup 1 nucleic acid in the sample. In additional embodiments, the methods further include detecting the presence of one or more of *Legionella bozemanii, Legionella dumoffii, Legionella feeleii, Legionella longbeachae, Legionella micdadei, Legionella sainthelensis, Legionella anisa, Legionella parisiensis*, and/or *Legionella tucsonensis* in a sample utilizing the methods described herein.

In another embodiment, the methods include contacting the sample with a first probe comprising a nucleic acid molecule between 10 and 40 nucleotides in length, wherein the first probe is capable of hybridizing under very high stringency conditions to a *Legionella bozemanii* gyrB nucleic acid sequence set forth as SEQ ID NO: 13; contacting the sample with a second probe comprising a nucleic acid molecule between 10 and 40 nucleotides in length, wherein the second probe is capable of hybridizing under very high stringency conditions to a *Legionella dumoffii* legS2 nucleic acid sequence set forth as SEQ ID NO: 14; contacting the sample with a third probe comprising a nucleic acid molecule between 10 and 40 nucleotides in length, wherein the third probe is capable of hybridizing under very high stringency conditions to a *Legionella feeleii* figA nucleic acid sequence set forth as SEQ ID NO: 15, contacting the sample with a fourth probe comprising a nucleic acid molecule between 10 and 40 nucleotides in length, wherein the third probe is capable of hybridizing under very high stringency conditions to a *Legionella longbeachae* ligB nucleic acid sequence set forth as SEQ ID NO: 16; and contacting the sample with a fifth probe comprising a nucleic acid molecule between 10 and 40 nucleotides in length, wherein the fifth probe is capable of hybridizing under very high stringency conditions to a *Legionella micdadei* migB nucleic acid sequence set forth as SEQ ID NO: 17; wherein each of the first, second, third, fourth, and fifth probes are detectably labeled; and the method further includes detecting hybridization between one or more probe and nucleic acid, wherein detection of hybridization between the first probe and a nucleic acid (such as SEQ ID NO: 13 or a portion thereof) indicates the presence of *Legionella bozemanii* nucleic acid in the sample, detection of hybridization between the second probe and a nucleic acid (such as SEQ ID NO: 14 or a portion thereof) indicates the presence of *Legionella dumoffii* nucleic acid in the sample, detection of hybridization between the third probe and a nucleic acid (such as SEQ ID NO: 15 or a portion thereof) indicates the presence of *Legionella feeleii* nucleic acid in the sample, detection of hybridization between the fourth probe and a nucleic acid (such as SEQ ID NO: 16 or a portion thereof) indicates the presence of *Legionella longbeachae* nucleic acid in the sample, and detection of hybridization between the fifth probe and a nucleic acid (such as SEQ ID NO: 17 or a portion thereof) indicates the presence of *Legionella micdadei* nucleic acid in the sample. In some examples, the sample is contacted with each of the probes in the same reaction, such as a multiplex PCR reaction. In other examples, the sample is contacted with each of the probes in separate reactions.

For example, in some embodiments the disclosed methods include contacting a sample with at least one of the probes (such as 1, 2, 3, 4, or 5 probes) disclosed herein (such as a nucleic acid probe capable of hybridizing under very high stringency conditions to a *Legionella bozemanii* gyrB nucleic acid sequence set forth as SEQ ID NO: 13, a *Legionella dumoffii* legS2 nucleic acid sequence set forth as SEQ ID NO: 14, a *Legionella feeleii* figA nucleic acid sequence set forth as SEQ ID NO: 15, a *Legionella longbeachae* ligB nucleic acid sequence set forth as SEQ ID NO: 16, and/or a *Legionella micdadei* migB nucleic acid sequence set forth as SEQ ID NO: 17, for example a nucleic acid sequence at least 90% identical to the nucleotide sequence set forth as one of SEQ ID NO: 20, SEQ ID NO: 23, SEQ ID NO: 26, SEQ ID NO: 29, or SEQ ID NOs: 32-36 (such as a nucleic acid sequence consisting essentially of the nucleic acid sequence set forth as one of SEQ ID NO: 20, SEQ ID NO: 23, SEQ ID NO: 26, SEQ ID NO: 29, or SEQ ID NOs: 32-36), and detecting hybridization between a nucleic acid and the respective probe. In particular examples, the probes are detectably labeled (for example, as described in section IV, below). Detection of hybridization between the *Legionella bozemanii* gyrB probe (for example SEQ ID NO: 20, SEQ ID NO: 33, or SEQ ID NO: 35) and a nucleic acid indicates the presence of *Legionella bozemanii* nucleic acid in the sample, detection of hybridization between the *Legionella dumoffii* legS2 probe (for example, SEQ ID NO: 23) and a nucleic acid indicates the presence of *Legionella dumoffii* nucleic acid in the sample, detection of hybridization between the *Legionella feeleii* figA probe (for example, SEQ ID NO: 26, SEQ ID NO: 34, or SEQ ID NO: 36) and a nucleic acid indicates the presence of *Legionella feeleii* nucleic acid in the sample, detection of hybridization between the *Legionella longbeachae* ligB probe (for example, SEQ ID NO: 29) and a nucleic acid indicates the presence of *Legionella longbeachae* nucleic acid in the sample, and detection of hybridization between the *Legionella micdadei* migB probe (for example SEQ ID NO: 32) and a nucleic acid indicates the presence of *Legionella micdadei* nucleic acid in the sample. In some examples, detection of hybridization between the *Legionella bozemanii* gyrB probe and a nucleic acid indicates the presence of one or more of *Legionella anisa, Legionella parisiensis*, and *Legionella tucsonensis* in the sample. In other examples, detection of hybridization between the *Legionella longbeachae* ligB probe and a nucleic acid indicates the presence of *Legionella sainthelensis* in the sample.

In some embodiments, the methods disclosed herein further include positive and/or negative controls. One of ordinary skill in the art can select suitable controls. In some examples, a negative control is a no template control (such as a reaction that includes all components except the nucleic acid sample). In other examples, a positive control includes a sample known to include nucleic acid from a particular pathogen. In further examples, a positive control includes an internal positive control, such as a human nucleic acid (for example, RNase P) when the sample is from a human subject. In other examples, a positive control includes a synthetic positive control (such as a combined positive control), for example, a nucleic acid molecule including forward primer, probe, and reverse primer sequences for one or more primer/probe sets included in the assay. A combined positive control may also include additional positive or negative controls, such as a human nucleic acid control (for example, RNase P), and/or a control for laboratory contamination (such as a primer/probe that is not included in the assay). See, e.g., Kodani and Winchell (*J. Clin. Microbiol.* 50:1057-1060, 2011; incorporated herein by reference) for exemplary methods for constructing a combined positive control.

In some embodiments, nucleic acids present in a sample (for example, one or more *Legionella* nucleic acids in a sample) are amplified prior to using a hybridization probe for detection. For instance, it can be advantageous to amplify a portion of one of more of the disclosed nucleic acids, and then detect the presence of the amplified nucleic acid, for example, to increase the number of nucleic acids that can be detected, thereby increasing the signal obtained. In other examples, nucleic acids present in the sample are amplified simultaneously or substantially simultaneously with contacting the sample with one or more probes (for example, as in real-time PCR methods). Specific nucleic acid primers can be used to amplify a region that is at least about 50, at least about 60, at least about 70, at least about 80 at least about 90, at least about 100, at least about 200, at least about 230, at least about 300, at least about 400, at least about 500, at least about 1000, at least about 2000, or more base pairs in length to produce amplified nucleic acids. In other examples, specific nucleic acid primers can be used to amplify a region that is about 50-3000 base pairs in length (for example, about 70-2000 base pairs, about 100-1000 base pairs, about 50-250 base pairs, about 300-500 base pairs, or about 1000-3000 base pairs in length).

Detecting the amplified product typically includes the use of labeled probes that are sufficiently complementary to and hybridize to the amplified nucleic acid sequence. Thus, the presence, amount, and/or identity of the amplified product can be detected by hybridizing a labeled probe, such as a fluorescently labeled probe, complementary to the amplified product. In one embodiment, the detection of a target nucleic acid sequence of interest, such as a *Legionella* spp. ssrA nucleic acid, a *Legionella pneumophila* mip nucleic acid, a *Legionella pneumophila* serogroup 1 wzm nucleic acid, a *Legionella bozemanii* gyrB nucleic acid, a *Legionella dumoffii* legS2 nucleic acid, a *Legionella feeleii* figA nucleic acid, a *Legionella longbeachae* ligB nucleic acid, and/or a *Legionella micdadei* migB nucleic acid includes the combined use of PCR amplification and a labeled probe such that the product is measured using real-time PCR (such as TaqMan® real-time PCR). In another embodiment, the detection of an amplified target nucleic acid sequence of interest includes the transfer of the amplified target nucleic acid to a solid support, such as a blot, for example a Northern blot, and probing the blot with a probe, for example a labeled probe, that is complementary to the amplified target nucleic acid sequence. In still further embodiments, the detection of amplified target nucleic acid sequence of interest includes the hybridization of a labeled amplified target nucleic acid to probes disclosed herein that are arrayed in a predetermined array with an addressable location and that are complementary to the amplified target nucleic acid.

Any nucleic acid amplification method can be used to detect the presence of one or more *Legionella* nucleic acids in a sample. In one specific, non-limiting example, polymerase chain reaction (PCR) is used to amplify the nucleic acid sequences. In other specific, non-limiting examples, real-time PCR, reverse transcriptase-polymerase chain reaction (RT-PCR), real-time reverse transcriptase-polymerase chain reaction (rt RT-PCR), ligase chain reaction, or transcription-mediated amplification (TMA) is used to amplify the nucleic acids. In a specific example, one or more (such as 1, 2, or 3) of *Legionella* ssp. ssrA nucleic acid, *Legionella pneumophila* mip nucleic acid, or *Legionella pneumophila* serogroup 1 wzm nucleic acid is amplified by real-time PCR (for example, multiplex real-time PCR), for example real-time TaqMan® PCR. Techniques for nucleic acid amplification are well-known to those of ordinary skill in the art.

Typically, at least two primers are utilized in the amplification reaction. In some examples, amplification of the *Legionella* ssp. ssrA nucleic acid involves contacting the *Legionella* spp. nucleic acid with one or more primers (such as two or more primers) that are capable of hybridizing to and directing the amplification of at least a portion of a *Legionella* ssp. ssrA nucleic acid sequence set forth as SEQ NO: 2, for example a primer that is least 90% identical (such as 91%, 92%, 93%, 94%, 95%, 96%, 97%, 98%, 99%, or 100% identical) to the nucleotide sequence set forth as one of SEQ ID NO: 4 or SEQ ID NO: 5. In one example, a *Legionella* spp. ssrA nucleic acid is amplified utilizing a pair of primers, such as a forward primer at least 90% identical to SEQ ID NO: 4 and a reverse primer at least 90% identical to SEQ ID NO: 5, such as a forward primer consisting of SEQ ID NO: 4 and a reverse primer consisting of SEQ ID NO: 5.

Amplification of the *Legionella pneumophila* mip nucleic acid involves contacting the *Legionella pneumophila* nucleic acid with one or more primers (such as two or more primers) that are capable of hybridizing to and directing the amplification of at least a portion of a *Legionella pneumophila* mip nucleic acid sequence set forth as SEQ NO: 1, for example a primer that is least 90% identical (such as 91%, 92%, 93%, 94%, 95%, 96%, 97%, 98%, 99%, or 100% identical) to the nucleotide sequence set forth as one of SEQ ID NO: 7 or SEQ ID NO: 8. In one example, a *Legionella pneumophila* mip nucleic acid is amplified utilizing a pair of primers, such as a forward primer at least 90% identical to SEQ ID NO: 7 and a reverse primer at least 90% identical to SEQ ID NO: 8, such as a forward primer consisting of SEQ ID NO: 7 and a reverse primer consisting of SEQ ID NO: 8.

Amplification of the *Legionella pneumophila* serogroup 1 wzm nucleic acid involves contacting the *Legionella pneumophila* serogroup 1 wzm nucleic acid with one or more primers (such as two or more primers) that are capable of hybridizing to and directing the amplification of at least a portion of a *Legionella pneumophila* serogroup 1 wzm nucleic acid sequence set forth as SEQ NO: 3, for example a primer that is least 90% identical (such as 91%, 92%, 93%, 94%, 95%, 96%, 97%, 98%, 99%, or 100% identical) to the nucleotide sequence set forth as one of SEQ ID NO: 10 or SEQ ID NO: 11. In one example, a *Legionella pneumophila* serogroup 1 wzm nucleic acid is amplified utilizing a pair of primers, such as a forward primer at least 90% identical to SEQ ID NO: 10 and a reverse primer at least 90% identical to SEQ ID NO: 11, such as a forward primer consisting of SEQ ID NO: 10 and a reverse primer consisting of SEQ ID NO: 11.

Amplification of the *Legionella bozemanii* gyrB nucleic acid involves contacting the *Legionella bozemanii* gyrB nucleic acid with one or more primers (such as two or more primers) that are capable of hybridizing to and directing the amplification of at least a portion of a *Legionella bozemanii* gyrB nucleic acid sequence set forth as SEQ NO: 13, for example a primer that is least 90% identical (such as 91%, 92%, 93%, 94%, 95%, 96%, 97%, 98%, 99%, or 100% identical) to the nucleotide sequence set forth as one of SEQ ID NO: 18 or SEQ ID NO: 19. In one example, a *Legionella bozemanii* gyrB nucleic acid is amplified utilizing a pair of primers, such as a forward primer at least 90% identical to SEQ ID NO: 18 and a reverse primer at least 90% identical to SEQ ID NO: 19, such as a forward primer consisting of SEQ ID NO: 18 and a reverse primer consisting of SEQ ID NO: 19. In some examples, primers at least 90% identical to SEQ ID NO: 18 and SEQ ID NO: 19 may also amplify a gyrB nucleic acid from one or more of *Legionella anisa, Legionella parisiensis*, and/or *Legionella tucsonensis* (for example serogroups 1 and/or 3).

Amplification of the *Legionella dumoffii* legS2 nucleic acid involves contacting the *Legionella dumoffii* legS2 nucleic acid with one or more primers (such as two or more primers) that are capable of hybridizing to and directing the amplification of at least a portion of a *Legionella dumoffii* legS2 nucleic acid sequence set forth as SEQ NO: 14, for example a primer that is least 90% identical (such as 91%, 92%, 93%, 94%, 95%, 96%, 97%, 98%, 99%, or 100% identical) to the nucleotide sequence set forth as one of SEQ ID NO: 21 or SEQ ID NO: 22. In one example, a *Legionella dumoffii* legS2 nucleic acid is amplified utilizing a pair of primers, such as a forward primer at least 90% identical to SEQ ID NO: 21 and a reverse primer at least 90% identical to SEQ ID NO: 22, such as a forward primer consisting of SEQ ID NO: 21 and a reverse primer consisting of SEQ ID NO: 22.

Amplification of the *Legionella feeleii* figA nucleic acid involves contacting the *Legionella feeleii* figA nucleic acid with one or more primers (such as two or more primers) that are capable of hybridizing to and directing the amplification of at least a portion of a *Legionella feeleii* figA nucleic acid sequence set forth as SEQ NO: 15, for example a primer that is least 90% identical (such as 91%, 92%, 93%, 94%, 95%, 96%, 97%, 98%, 99%, or 100% identical) to the nucleotide sequence set forth as one of SEQ ID NO: 24 or SEQ ID NO: 25. In one example, a *Legionella feeleii* figA nucleic acid is amplified utilizing a pair of primers, such as a forward primer at least 90% identical to SEQ ID NO: 24 and a reverse primer at least 90% identical to SEQ ID NO: 25, such as a forward primer consisting of SEQ ID NO: 24 and a reverse primer consisting of SEQ ID NO: 25.

Amplification of the *Legionella longbeachae* ligB nucleic acid involves contacting the *Legionella longbeachae* ligB nucleic acid with one or more primers (such as two or more primers) that are capable of hybridizing to and directing the amplification of at least a portion of a *Legionella longbeachae* ligB nucleic acid sequence set forth as SEQ NO: 16, for example a primer that is least 90% identical (such as 91%, 92%, 93%, 94%, 95%, 96%, 97%, 98%, 99%, or 100% identical) to the nucleotide sequence set forth as one of SEQ ID NO: 27 or SEQ ID NO: 28. In one example, a *Legionella longbeachae* ligB nucleic acid is amplified utilizing a pair of primers, such as a forward primer at least 90% identical to SEQ ID NO: 27 and a reverse primer at least 90% identical to SEQ ID NO: 28, such as a forward primer consisting of SEQ ID NO: 27 and a reverse primer consisting of SEQ ID NO: 28. In some examples primers at least 90% identical to SEQ ID NO: 27 and SEQ ID NO: 28 may also amplify a ligB nucleic acid from *Legionella sainthelensis* (such as serogroup 1 or 2).

Amplification of the *Legionella micdadei* migB nucleic acid involves contacting the *Legionella micdadei* migB nucleic acid with one or more primers (such as two or more primers) that are capable of hybridizing to and directing the amplification of at least a portion of a *Legionella micdadei* migB nucleic acid sequence set forth as SEQ NO: 17, for example a primer that is least 90% identical (such as 91%, 92%, 93%, 94%, 95%, 96%, 97%, 98%, 99%, or 100% identical) to the nucleotide sequence set forth as one of SEQ ID NO: 30 or SEQ ID NO: 31. In one example, a *Legionella micdadei* migB nucleic acid is amplified utilizing a pair of primers, such as a forward primer at least 90% identical to SEQ ID NO: 30 and a reverse primer at least 90% identical to SEQ ID NO: 31, such as a forward primer consisting of SEQ ID NO: 30 and a reverse primer consisting of SEQ ID NO: 31. The amplified *Legionella* nucleic acids can be detected in real-time, for example by real-time PCR, in order to determine the presence, and/or the amount of *Legionella* spp., *Legionella pneumophila, Legionella pneumophila* serogroup 1, *Legionella bozemanii, Legionella dumoffii, Legionella feeleii, Legionella longbeachae, Legionella micdadei, Legionella sainthelensis, Legionella anisa, Legionella parisiensis*, and/or *Legionella tucsonensis* specific nucleic acid in a sample. In this manner, an amplified nucleic acid can be detected using a probe specific for the product amplified from the target sequence of interest, such as an amplified *Legionella* spp. ssrA nucleic acid, *Legionella pneumophila* mip nucleic acid, *Legionella pneumophila* serogroup 1 wzm nucleic acid, *Legionella bozemanii* gyrB nucleic acid, *Legionella dumoffii* legS2 nucleic acid, *Legionella feeleii* figA nucleic acid, *Legionella longbeachae* ligB nucleic acid, or *Legionella micdadei* migB nucleic acid. Suitable probes for real-time PCR include those described herein, such as a probe having a nucleic acid sequence at least 90% identical to SEQ ID NOs: 6, 9, 12, 20, 23, 26, 29, or 32. In particular examples of the disclosed methods, multiplex real-time PCR is utilized to detect and/or discriminate *Legionella* spp., *Legionella pneumophila* and/or *Legionella pneumophila* serogroup 1 nucleic acid present in the sample. In additional examples of the disclosed methods, multiplex real-time PCR is utilized to detect and/or discriminate *Legionella bozemanii, Legionella dumoffii, Legionella feeleii, Legionella longbeachae, Legionella micdadei, Legionella sainthelensis, Legionella anisa, Legionella parisiensis*, and/or *Legionella tucsonensis* nucleic acid present in the sample.

Real-time PCR monitors the fluorescence emitted during the reaction as an indicator of amplicon production during each PCR cycle, as opposed to endpoint detection. The real-time progress of the reaction can be viewed in some systems. Typically, real-time PCR uses the detection of a fluorescent reporter. Typically, the fluorescent reporter's signal increases in direct proportion to the amount of PCR product in a reaction. By recording the amount of fluorescence emission at each cycle, it is possible to monitor the PCR reaction during exponential phase where the first significant increase in the amount of PCR product correlates to the initial amount of target template. The higher the starting copy number of the nucleic acid target, the sooner a significant increase in fluorescence is observed.

In one embodiment, the fluorescently-labeled probes (such as probes disclosed herein) rely upon fluorescence resonance energy transfer (FRET), or in a change in the fluorescence emission wavelength of a sample, as a method to detect hybridization of a DNA probe to the amplified target nucleic acid in real-time. For example, FRET that occurs between fluorogenic labels on different probes (for example, using HybProbes) or between a donor fluorophore and an acceptor or quencher fluorophore on the same probe (for example, using a molecular beacon or a TaqMan® probe) can identify a probe that specifically hybridizes to the DNA sequence of interest and in this way, can detect the presence, and/or amount of the respective nucleic acid in a sample.

In some embodiments, the fluorescently-labeled DNA probes used to identify amplification products have spectrally distinct emission wavelengths, thus allowing them to be distinguished within the same reaction tube, for example in multiplex PCR, such as a multiplex real-time PCR. In some embodiments, the probes and primers disclosed herein are used in multiplex real-time PCR. For example, multiplex PCR permits the simultaneous detection of the amplification products of a *Legionella* spp. ssrA nucleic acid, a *Legionella pneumophila* mip nucleic acid, and/or a *Legionella pneumophila* serogroup 1 wzm nucleic acid using the disclosed probes or even another nucleic acid, such as a control nucleic acid. For example, multiplex PCR permits the simultaneous detection of the amplification products of a *Legionella bozemanii* gyrB nucleic acid, *Legionella dumoffii* legS2 nucleic acid, *Legionella feeleii* figA nucleic acid, *Legionella longbeachae* ligB nucleic acid, *Legionella micdadei* migB nucleic acid, *Legionella sainthelensis* ligB nucleic acid, and/or a *Legionella anisa, Legionella parisiensis*, and/or *Legionella tucsonensis* gyrB nucleic acid using the disclosed probes or even another nucleic acid, such as a control nucleic acid. Using the disclosed primers and probes, any combination of *Legionella* spp., *Legionella pneumophila, Legionella pneumophila* serogroup 1, *Legionella bozemanii, Legionella dumoffii, Legionella feeleii, Legionella longbeachae, Legionella micdadei, Legionella sainthelensis, Legionella anisa, Legionella parisiensis*, and *Legionella tucsonensis* nucleic acids can be detected.

In other examples, the probes and primers disclosed herein are used in a bead-based multiplex assay (see, e.g., U.S. Pat. No. 6,939,720). For example, *Legionella*-specific probes (such as the probes disclosed herein), which are attached to different fluorescently labeled beads, are hybridized to amplified DNA from the sample. The probes will only significantly hybridize if the particular *Legionella* nucleic acid is present in the sample. The hybridized beads are then captured, for example with a biotinylated detector molecule, and the relative fluorescence of the beads for each label is measured.

In another embodiment, a melting curve analysis of the amplified target nucleic acid can be performed subsequent to the amplification process. The $T_m$ of a nucleic acid sequence depends on the length of the sequence and its G/C content. Thus, the identification of the $T_m$ for a nucleic acid sequence can be used to identify the amplified nucleic acid, for example by using double-stranded DNA binding dye chemistry, which quantitates the amplicon production by the use of a non-sequence specific fluorescent intercalating agent (such as SYBR® Green or ethidium bromide). SYBR® Green is a fluorogenic minor groove binding dye that exhibits little fluorescence when in solution but emits a strong fluorescent signal upon binding to double-stranded DNA. Typically, SYBR® Green is used in singleplex reactions, however when coupled with melting point analysis, it can be used for multiplex reactions.

Any type of thermal cycler apparatus can be used for the amplification of nucleic acids and/or the determination of hybridization. Examples of suitable apparatuses include PTC-100® Peltier Thermal Cycler (MJ Research, Inc.; San Francisco, Calif.), a RoboCycler® 40 Temperature Cycler (Agilent/Stratagene; Santa Clara, Calif.), or GeneAmp® PCR System 9700 (Applied Biosystems; Foster City, Calif.). For real-time PCR, any type of real-time thermocycler apparatus can be used. For example, iCycler iQ™ or CFX96™ real-time detection systems (Bio-Rad, Hercules, Calif.), LightCycler® systems (Roche, Mannheim, Germany), a 7700 Sequence Detector (Perkin Elmer/Applied Biosystems; Foster City, Calif.), ABI™ systems such as the 7000, 7300, 7500, 7700, or 7900 systems (Applied Biosystems; Foster City, Calif.), or an MX4000™, MX3000™ or MX3005™ qPCR system (Agilent/Stratagene; Santa Clara, Calif.), DNA Engine Opticon® Continuous Fluorescence Detection System (Bio-Rad, Hercules, Calif.), Rotor-Gene® Q real-time cycler (Qiagen, Valencia, Calif.), or SmartCycler® system (Cepheid, Sunnyvale, Calif.) can be used to amplify nucleic acid sequences in real-time. In some embodiments, real-time PCR is performed using a TaqMan® array format, for example, a microfluidic card in which each well is pre-loaded with primers and probes for a particular target. The reaction is initiated by adding a sample including nucleic acids and assay reagents (such as a PCR master mix) and running the reactions in a real-time thermocycler apparatus.

In some embodiments, the probe is detectably labeled, either with an isotopic or non-isotopic label; in alternative embodiments, the target nucleic acid is labeled. Non-isotopic labels can, for instance, comprise a fluorescent or luminescent molecule, or an enzyme, co-factor, enzyme substrate, or hapten. The probe is incubated with a single-stranded or double-stranded preparation of RNA, DNA, or a mixture of both, and hybridization is determined. In some examples, the hybridization results in a detectable change in signal such as in increase or decrease in signal, for example from the labeled probe. Thus, detecting hybridization comprises detecting a change in signal from the labeled probe during or after hybridization relative to signal from the label before hybridization.

In some examples, the disclosed methods can predict with a sensitivity of at least 80% and a specificity of at least 80% for presence of any of a *Legionella* spp. nucleic acid, a *Legionella pneumophila* nucleic acid, a *Legionella pneumophila* serogroup 1 nucleic acid, a *Legionella bozemanii* nucleic acid, a *Legionella dumoffii* nucleic acid, a *Legionella feeleii* nucleic acid, a *Legionella longbeachae* nucleic acid, a *Legionella micdadei* nucleic acid, a *Legionella sainthelensis* nucleic acid, a *Legionella anisa* nucleic acid, a *Legionella parisiensis* nucleic acid, or a *Legionella tucsonensis* nucleic acid, such as a sensitivity of at least 81%, 82%, 83%, 84%, 85%, 86%, 87%, 88%, 89%, 90%, 91%, 92%, 93%, 94%, 95%, 96%, 97%, 98%, 99%, or even 100% and a specificity of at least of at least 81%, 82%, 83%, 84%, 85%, 86%, 87%, 88%, 89%, 90%, 91%, 92%, 93%, 94%, 95%, 96%, 97%, 98%, 99%, or even 100%.

IV. Probes and Primers

Probes and primers suitable for use in the disclosed methods are described herein. Such probes and primers include nucleic acid molecules capable of hybridizing to the disclosed nucleic acid molecules, such as any one of SEQ ID NOs: 1-3 or 13-17.

A. Probes

Probes capable of hybridizing to and detecting the presence of *Legionella* spp., *Legionella pneumophila*, and/or *Legionella pneumophila* serogroup 1 nucleic acid molecules, such as *Legionella* spp. ssrA nucleic acid molecules, *Legionella pneumophila* mip nucleic acid molecules, *Legionella pneumophila* serogroup 1 wzm nucleic acid molecules, *Legionella bozemanii* gyrB nucleic acid molecules, *Legionella dumoffii* legS2 nucleic acid molecules, *Legionella feeleii* figA nucleic acid molecules, *Legionella longbeachae* ligB nucleic acid molecules, or *Legionella micdadei* migB nucleic acid molecules are disclosed. In some embodiments, the disclosed probes are between 10 and 40 nucleotides in length, such as 10, 11, 12, 13, 14, 15, 16, 17, 18, 19, 20, 21, 22, 23, 24, 25, 26, 27, 28 29, 30, 31, 32, 32, 34, 35, 36, 37, 38, 39, or 40 nucleotides in length and are capable of hybridizing to the disclosed nucleic acid molecules (such as SEQ ID NOs: 1-3 or 13-17). In some examples, the probes are at least 10, 15, 20, 25, 30, 35, or 40 nucleotides in length. In other examples, the probes may be no more than 10, 15, 20, 25, 30, 35, or 40 nucleotides in length.

In several embodiments, a probe is capable of hybridizing under high or very high stringency conditions to a *Legionella* spp. nucleic acid sequence set forth as SEQ ID NO: 2. In some examples, a probe capable of hybridizing to a *Legionella* spp. ssrA nucleic molecule includes a nucleic acid sequence that is at least 90% identical, such as at least 91%, 92%, 93%, 94%, 95%, 96%, 97%, 98%, 99%, or even 100% identical, to the nucleotide sequence set forth as CGTGGGTTGCAA (SEQ ID NO: 6). In several embodiments, a probe capable of hybridizing to a *Legionella* spp. ssrA nucleic acid molecule consists essentially of, or consists of, a nucleic acid sequence set forth as SEQ ID NO: 6. In particular embodiments, the probe capable of hybridizing to a *Legionella* spp. ssrA nucleic acid molecule is capable of hybridizing to an ssrA nucleic acid molecule from any *Legionella* species or serogroup (such as those shown in Table 2 (below), for example, *L. pneumophila* (such as *L. pneumophila* serogroups Sg1, Sg2, Sg4, and Sg6), *L. bozemanii, L. longbeachae, L. micdadei, L. birminghamensis, L. dumoffii, L. hackliae, L. maceachernii, L. wadsworthii, L. jordanis, L. feeleii, L. cincinnatiensis, L. gormanii, L. sainthelensis, L. tucsonensis, L. anisa, L. lansingensis, L. erythra, L. parisiensis, L. oakridgensis, L. spiritensis, L. jamestowniensis, L. santicrucis, L. cherrii, L. steigerwaltii, L. rubrilucens, L. israelensis, L. quinlivanii, L. brunensis, L. moravica, L. gratiana, L. adelaidensis, L. fairfieldensis, L. shakespearei, L. waltersii, L. genomospecies, L. quateirensis, L. worsleiensis, L. geestiana, L. natarum, L. londoniensis, L. taurinensis, L. lytica, L. drozanskii, L. rowbothamii, L. fallonii, L. gresilensis*, and *L. beliardensis*).

In several embodiments, a probe is capable of hybridizing under high or very high stringency conditions to a *Legionella pneumophila* nucleic acid sequence set forth as SEQ ID NO: 1. In some examples, a probe capable of hybridizing to a *Legionella pneumophila* mip nucleic molecule includes a nucleic acid sequence that is at least 90% identical, such as at least 91%, 92%, 93%, 94%, 95%, 96%, 97%, 98%, 99%, or even 100% identical, to the nucleotide sequence set forth as CGGAAGCAATGGCTAAAGGCATGCA (SEQ ID NO: 9). In several embodiments, a probe capable of hybridizing to a *Legionella pneumophila* mip nucleic acid molecule consists essentially of, or consists of, a nucleic acid sequence set forth as SEQ ID NO: 9. In particular embodiments, the probe capable of hybridizing to a *Legionella pneumophila* mip nucleic acid molecule is capable of hybridizing to a mip nucleic acid molecule from any *Legionella pneumophila* serogroup (for example, *Legionella pneumophila* serogroups Sg1, Sg2, Sg3, Sg4, Sg5, Sg6, Sg7, Sg8, Sg9, Sg10, Sg11, Sg12, Sg13, or Sg14).

In several embodiments, a probe is capable of hybridizing under high or very high stringency conditions to a *Legionella pneumophila* serogroup 1 nucleic acid sequence set forth as SEQ ID NO: 3. In some examples, a probe capable of hybridizing to a *Legionella pneumophila* serogroup 1 wzm nucleic molecule includes a nucleic acid sequence that is at least 90% identical, such as at least 91%, 92%, 93%, 94%, 95%, 96%, 97%, 98%, 99%, or even 100% identical, to the nucleotide sequence set forth as TTTATTACTCCACTCCAGCGAT (SEQ ID NO: 12). In several embodiments, a probe capable of hybridizing to a *Legionella pneumophila* serogroup 1 wzm nucleic acid molecule consists essentially of, or consists of, a nucleic acid sequence set forth as SEQ ID NO: 12. In particular embodiments, the probe capable of hybridizing to a *Legionella pneumophila* serogroup 1 wzm nucleic acid molecule is capable of hybridizing to a wzm nucleic acid molecule from *Legionella pneumophila* serogroup 1, but not a wzm nucleic acid molecule from other *Legionella pneumophila* serogroups (for example, *Legionella pneumophila* serogroups Sg2, Sg3, Sg4, Sg5, Sg6, Sg7, Sg8, Sg9, Sg10, Sg11, Sg12, Sg13, or Sg14).

In several embodiments, a probe is capable of hybridizing under high or very high stringency conditions to a *Legionella bozemanii* nucleic acid sequence set forth as SEQ ID NO: 13. In some examples, a probe capable of hybridizing to a *Legionella bozemanii* gyrB nucleic acid molecule includes a nucleic acid sequence that is at least 90% identical, such as at least 91%, 92%, 93%, 94%, 95%, 96%, 97%, 98%, 99%, or even 100% identical, to the nucleotide sequence set forth as GTGCTTCACGCCGGTGGTAAATTT (SEQ ID NO: 20), TGCTTCACGCCGGTGGTAAATTTG (SEQ ID NO: 33), or AAATTTACCACCGGCGTGAAGCAC (SEQ ID NO: 35). In several embodiments, a probe capable of hybridizing to a *Legionella bozemanii* gyrB nucleic acid molecule consists essentially of, or consists of, a nucleic acid sequence set forth as SEQ ID NO: 20, SEQ ID NO: 33, or SEQ ID NO: 35. In particular embodiments, the probe capable of hybridizing to a *Legionella bozemanii* gyrB nucleic acid molecule is also capable of hybridizing to a gyrB nucleic acid molecule from *Legionella anisa, Legionella parisiensis*, and/or *Legionella tucsonensis.*

In several embodiments, a probe is capable of hybridizing under high or very high stringency conditions to a *Legionella dumoffii* nucleic acid sequence set forth as SEQ ID NO: 14. In some examples, a probe capable of hybridizing to a *Legionella dumoffii* legS2 nucleic acid molecule includes a nucleic acid sequence that is at least 90% identical, such as at least 91%, 92%, 93%, 94%, 95%, 96%, 97%, 98%, 99%, or even 100% identical, to the nucleotide sequence set forth as TGGAAACCCTCAATGGTCCGTTCT (SEQ ID NO: 23). In several embodiments, a probe capable of hybridizing to a *Legionella dumoffii* legS2 nucleic acid molecule consists essentially of, or consists of, a nucleic acid sequence set forth as SEQ ID NO: 23.

In several embodiments, a probe is capable of hybridizing under high or very high stringency conditions to a *Legionella feeleii* nucleic acid sequence set forth as SEQ ID NO: 15. In some examples, a probe capable of hybridizing to a *Legionella feeleii* figA nucleic acid molecule includes a nucleic acid sequence that is at least 90% identical, such as at least 91%, 92%, 93%, 94%, 95%, 96%, 97%, 98%, 99%, or even 100% identical, to the nucleotide sequence set forth as GCGAGTGATAATCCATCAAATTCTCAAGCT (SEQ ID NO: 26), AGCGAGTGATAATCCATCAAATTCTCAAGC (SEQ ID NO: 34), or AGCTTGAGAATTTGATGGATTAT-CACTCGC (SEQ ID NO:36). In several embodiments, a probe capable of hybridizing to a *Legionella feeleii* figA nucleic acid molecule consists essentially of, or consists of, a nucleic acid sequence set forth as SEQ ID NO: 26, SEQ ID NO: 34, or SEQ ID NO: 36.

In several embodiments, a probe is capable of hybridizing under high or very high stringency conditions to a *Legionella longbeachae* nucleic acid sequence set forth as SEQ ID NO: 16. In some examples, a probe capable of hybridizing to a *Legionella longbeachae* ligB nucleic acid molecule includes a nucleic acid sequence that is at least 90% identical, such as at least 91%, 92%, 93%, 94%, 95%, 96%, 97%, 98%, 99%, or even 100% identical, to the nucleotide sequence set forth as TGTCGCCAAGAAGTTGTATCTCATGCT (SEQ ID NO: 29). In several embodiments, a probe capable of hybridizing to a *Legionella longbeachae* ligB nucleic acid molecule consists essentially of, or consists of, a nucleic acid sequence set forth as SEQ ID NO: 29. In particular embodiments, the probe capable of hybridizing to a *Legionella longbeachae* ligB nucleic acid molecule is also capable of hybridizing to a ligB nucleic acid molecule from *Legionella sainthelensis.*

In several embodiments, a probe is capable of hybridizing under high or very high stringency conditions to a *Legionella micdadei* nucleic acid sequence set forth as SEQ ID NO: 17. In some examples, a probe capable of hybridizing to a *Legionella micdadei* migB nucleic acid molecule includes a nucleic acid sequence that is at least 90% identical, such as at least 91%, 92%, 93%, 94%, 95%, 96%, 97%, 98%, 99%, or even 100% identical, to the nucleotide sequence set forth as ACAGAAGGAGAACCTTCCGGTGTG (SEQ ID NO: 32). In several embodiments, a probe capable of hybridizing to a *Legionella micdadei* migB nucleic acid molecule consists essentially of, or consists of, a nucleic acid sequence set forth as SEQ ID NO: 32.

In particular embodiments, the probe is detectably labeled, either with an isotopic or non-isotopic label. Non-isotopic labels can include a fluorescent or luminescent molecule, a hapten (such as biotin, dinitrophenyl, or digoxigenin), an enzyme or enzyme substrate or a chemical. Such labels are preferentially chosen such that the hybridization of the probe with a target nucleic acid can be detected.

In some examples, the probe is labeled with one or more fluorophores. Examples of suitable fluorophore labels are provided above. In some examples, the fluorophore is a donor fluorophore. In other examples, the fluorophore is an accepter fluorophore, such as a fluorescence quencher. In some examples, the probe includes both a donor fluorophore and an accepter fluorophore (such as a dark quencher), for example a donor fluorophore such as FAM or VIC and a quencher such as a BLACK HOLE® quencher. One of ordinary skill in the art can select appropriate donor/acceptor fluorophore or donor/dark quencher pairs. In one example, the donor emission wavelength is one that can significantly excite the acceptor, thereby generating a detectable emission from the acceptor. In some examples, the probe is modified at the 3'-end to prevent extension of the probe by a polymerase.

In some examples, the acceptor fluorophore (such as a fluorescence quencher) is attached to the 3' end of the probe and the donor fluorophore is attached to a 5' end of the probe. In other examples, the acceptor fluorophore (such as a fluorescence quencher) is attached to the 5' end of the probe and the donor fluorophore is attached to a 3' end of the probe. In another particular example, the acceptor fluorophore (such as a fluorescence quencher) is attached to a modified nucleotide (such as a T) and the donor fluorophore is attached to a 5' end of the probe.

In particular embodiments, the probe capable of hybridizing to a *Legionella* spp. ssrA nucleic molecule includes a donor fluorophore attached to the 5' end and an acceptor fluorophore (quencher) attached to the 3' end. In one example, the *Legionella* spp. ssrA probe includes the donor fluorophore FAM and the acceptor fluorophore minor groove binder/non-fluorescent quencher (MGBNFQ). In a particular example, the *Legionella* spp. ssrA probe consists of FAM-CGTGGGTTGCAA-MGBNFQ (SEQ ID NO: 6).

In additional embodiments, the probe capable of hybridizing to a *Legionella pneumophila* mip nucleic molecule includes a donor fluorophore attached to the 5' end and an acceptor fluorophore attached to the 3' end. In one example, the *Legionella pneumophila* mip probe includes the donor fluorophore Quasar 670 and the acceptor fluorophore BHQ3. In a particular example, the *Legionella pneumophila* mip probe consists of Quasar 670-CGGAAGCAATGGCTAAAGGCATGCA-BHQ3 (SEQ ID NO: 9).

In further embodiments, the probe capable of hybridizing to a *Legionella pneumophila* serogroup 1 wzm nucleic molecule includes a donor fluorophore attached to the 5' end and an acceptor fluorophore attached to the 3' end. In one example, the *Legionella pneumophila* serogroup 1 wzm probe includes the donor fluorophore VIC and the acceptor fluorophore MGBNFQ. In a particular example, the *Legionella pneumophila* serogroup 1 wzm probe consists of VIC-TTTATTACTCCACTCCAGCGAT-MGBNFQ (SEQ ID NO: 12).

In additional embodiments, the probe capable of hybridizing to a *Legionella bozemanii* gyrB nucleic molecule includes a donor fluorophore attached to the 5' end and an acceptor fluorophore attached to the 3' end. In one example, the *Legionella bozemanii* gyrB probe includes the donor fluorophore Quasar 705 and the acceptor fluorophore BHQ3. In a particular example, the *Legionella bozemanii* gyrB probe consists of Quasar 705-GTGCTTCACGCCGGTGGTAAATTT-BHQ3 (SEQ ID NO: 20), Quasar 705-TGCTTCACGCCGGTGGTAAATTTG-BHQ3 (SEQ ID NO: 33), or Quasar 705-AAATTTACCACCGGCGTGAAGCAC-BHQ3 (SEQ ID NO: 35).

In additional embodiments, the probe capable of hybridizing to a *Legionella dumoffii* legS2 nucleic molecule includes a donor fluorophore attached to the 5' end and an acceptor fluorophore attached to the 3' end. In one example, the *Legionella dumoffii* legS2 probe includes the donor fluorophore HEX and the acceptor fluorophore BHQ1. In a particular example, the *Legionella dumoffii* legS2 probe consists of HEX-TGGAAACCCTCAATGGTCCGTTCT-BHQ1 (SEQ ID NO: 23).

In additional embodiments, the probe capable of hybridizing to a *Legionella* feeleii figA nucleic molecule includes a donor fluorophore attached to the 5' end and an acceptor fluorophore attached to the 3' end. In one example, the *Legionella feeleii* figA probe includes the donor fluorophore TexasRed 615 and the acceptor fluorophore BHQ2. In a particular example, the *Legionella feeleii* figA probe consists of TexasRed 615-GCGAGTGATAATCCATCAAATTCTCAAGCT-BHQ2 (SEQ ID NO: 26), TexasRed 615-AGCGAGTGATAATCCATCAAATTCTCAAGC-BHQ2 (SEQ ID NO: 34), or TexasRed 615-AGCTTGAGAATTTGATGGATTATCACTCGC-BHQ2 (SEQ ID NO: 36).

In additional embodiments, the probe capable of hybridizing to a *Legionella longbeachae* ligB nucleic molecule includes a donor fluorophore attached to the 5' end and an acceptor fluorophore attached to the 3' end. In one example, the *Legionella longbeachae* ligB probe includes the donor fluorophore Quasar 670 and the acceptor fluorophore BHQ3. In a particular example, the *Legionella longbeachae* ligB probe consists of Quasar 670-TGTCGCCAAGAAGTTGTATCTCATGCT-BHQ3 (SEQ ID NO: 29).

In additional embodiments, the probe capable of hybridizing to a *Legionella micdadei* migB nucleic molecule includes a donor fluorophore attached to the 5' end and an acceptor fluorophore attached to the 3' end. In one example, the *Legionella micdadei* migB probe includes the donor fluorophore FAM and the acceptor fluorophore BHQ1. In a particular example, the *Legionella micdadei* migB probe consists of FAM-ACAGAAGGAGAACCTTCCGGTGTG-BHQ1 (SEQ ID NO: 32).

B. Primers

Primers capable of hybridizing to and directing the amplification of a *Legionella* spp. ssrA nucleic acid molecule, a *Legionella pneumophila* mip nucleic acid molecule, a *Legionella pneumophila* serogroup 1 wzm nucleic acid molecule, a *Legionella bozemanii* gyrB nucleic acid molecule, a *Legionella dumoffii* legS2 nucleic acid molecule, a *Legionella feeleii* figA nucleic acid molecule, a *Legionella longbeachae* ligB nucleic acid molecule, or a *Legionella micdadei* migB nucleic acid molecule are also disclosed. The primers disclosed herein are between 10 to 40 nucleotides in length, such as 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or even 40 nucleotides in length. In some examples, the primers are at least 10, 15, 20, 25, 30, 35, or 40 nucleotides in length. In other examples, the primers may be no more than 10, 15, 20, 25, 30, 35, or 40 nucleotides in length.

In several embodiments, a primer is capable of hybridizing under high or very high stringency conditions to a *Legionella* ssp. ssrA nucleic acid sequence, such as a *Legionella* spp. ssrA nucleic acid sequence set forth as SEQ ID NO: 2, and directing the amplification of the *Legionella* spp. ssrA nucleic acid molecule, for example amplification of SEQ ID NO: 2 or a subsequence thereof. In several embodiments, a primer is capable of hybridizing under high or very high stringency conditions to a *Legionella pneumophila* mip nucleic acid sequence, such as a *Legionella pneumophila* mip nucleic acid sequence set forth as SEQ ID NO: 1, and directing the amplification of the *Legionella pneumophila* mip nucleic acid molecule, for example amplification of SEQ ID NO: 1 or a subsequence thereof. In several embodiments, a primer is capable of hybridizing under high or very high stringency conditions to a *Legionella pneumophila* serogroup 1 wzm nucleic acid sequence, such as a *Legionella pneumophila* serogroup 1 wzm nucleic acid sequence set forth as SEQ ID NO: 3, and directing the amplification of the *Legionella pneumophila* serogroup 1 wzm nucleic acid molecule, for example amplification of SEQ ID NO: 3 or a subsequence thereof. In several embodiments, a primer is capable of hybridizing under high or very high stringency conditions to a *Legionella bozemanii* gyrB nucleic acid sequence, such as a *Legionella bozemanii* gyrB nucleic acid sequence set forth as SEQ ID NO: 13, and directing the amplification of the *Legionella bozemanii* gyrB nucleic acid molecule, for example amplification of SEQ ID NO: 13 or a subsequence thereof. In additional embodiments, a primer is capable of hybridizing under high or very high stringency conditions to a *Legionella dumoffii* legS2 nucleic acid sequence, such as a *Legionella dumoffii* legS2 nucleic acid sequence set forth as SEQ ID NO: 14, and directing the amplification of the *Legionella dumoffii* legS2 nucleic acid molecule, for example amplification of SEQ ID NO: 14 or a subsequence thereof. In several embodiments, a primer is capable of hybridizing under high or very high stringency conditions to a *Legionella feeleii* figA nucleic acid sequence, such as a *Legionella feeleii* figA nucleic acid sequence set forth as SEQ ID NO: 15, and directing the amplification of the *Legionella feeleii* figA nucleic acid molecule, for example amplification of SEQ ID NO: 15 or a subsequence thereof. In several embodiments, a primer is capable of hybridizing under high or very high stringency conditions to a *Legionella longbeachae* ligB nucleic acid sequence, such as a *Legionella longbeachae* ligB nucleic acid sequence set forth as SEQ ID NO: 16, and directing the amplification of the *Legionella longbeachae* ligB nucleic acid molecule, for example amplification of SEQ ID NO: 16 or a subsequence thereof. In several embodiments, a primer is capable of hybridizing under high or very high stringency conditions to a *Legionella micdadei* migB nucleic acid sequence, such as a *Legionella micdadei* migB nucleic acid sequence set forth as SEQ ID NO: 17, and directing the amplification of the *Legionella micdadei* migB nucleic acid molecule, for example amplification of SEQ ID NO: 17 or a subsequence thereof.

In several embodiments, a primer capable of hybridizing to and directing the amplification of a *Legionella* ssp. ssrA nucleic acid molecule includes a nucleic acid sequence that is at least 90% identical, such as at least 91%, 92%, 93%, 94%, 95%, 96%, 97%, 98%, 99%, or even 100% identical, to the nucleic acid sequence set forth as GGCGACCTGGCTTC (SEQ ID NO: 4) or GGTCATCGTTTGCATTTATATTTA (SEQ ID NO: 5). In several embodiments, a primer capable of hybridizing to and directing the amplification of a *Legionella* ssp. ssrA nucleic acid molecule consists essentially of, or consists of a nucleic acid sequence set forth as SEQ ID NO: 4 or SEQ ID NO: 5. In particular embodiments, the primer capable of hybridizing to and directing amplification of a *Legionella* spp. ssrA nucleic acid molecule (such as SEQ ID NO: 4 or SEQ ID NO: 5) is capable of hybridizing to an ssrA nucleic acid molecule from any *Legionella* species (such as those shown in Table 2 (below), for example, *L. pneumophila* (such as *L. pneumophila* subtypes Sg1, Sg2, Sg4, and Sg6), *L. bozemanii, L. longbeachae, L. micdadei, L. birminghamensis, L. dumoffii, L. hackliae, L. maceachernii, L. wadsworthii, L. jordanis, L. feeleii, L. cincinnatiensis, L. gormanii, L. sainthelensis, L. tucsonensis, L. anisa, L. lansingensis, L. erythra, L. parisiensis, L. oakridgensis, L. spiritensis, L. jamestowniensis, L. santicrucis, L. cherrii, L. steigerwaltii, L. rubrilucens, L. israelensis, L. quinlivanii, L. brunensis, L. moravica, L. gratiana, L. adelaidensis, L. fairfieldensis, L. shakespearei, L. waltersii, L. genomospecies, L. quateirensis, L. worsleiensis, L. geestiana, L. natarum, L. londoniensis, L. taurinensis, L. lytica, L. drozanskii, L. rowbothamii, L. fallonii, L. gresilensis*, and *L. beliardensis*).

In several embodiments, a primer capable of hybridizing to and directing the amplification of a *Legionella pneumophila* mip nucleic acid molecule includes a nucleic acid sequence that is at least 90% identical, such as at least 91%, 92%, 93%, 94%, 95%, 96%, 97%, 98%, 99%, or even 100% identical, to the nucleic acid sequence set forth as TTGTCTTATAGCATTGGTGCCG (SEQ ID NO: 7) or CCAATTGAGCGCCACTCATAG (SEQ ID NO: 8). In several embodiments, a primer capable of hybridizing to and directing the amplification of a *Legionella pneumophila* mip nucleic acid molecule consists essentially of, or consists of a nucleic acid sequence set forth as SEQ ID NO: 7 or SEQ ID NO: 8. In particular embodiments, the primer capable of hybridizing to and directing amplification of a *Legionella pneumophila* mip nucleic acid molecule (such as SEQ ID NO: 7 or SEQ ID NO: 8) is capable of hybridizing to a mip nucleic acid molecule from any *Legionella pneumophila* serogroup (for example, *Legionella pneumophila* serogroups Sg1, Sg2, Sg3, Sg4, Sg5, Sg6, Sg7, Sg8, Sg9, Sg10, Sg11, Sg12, Sg13, or Sg14).

In several embodiments, a primer capable of hybridizing to and directing the amplification of a *Legionella pneumophila* serogroup 1 wzm nucleic acid molecule includes a nucleic acid sequence that is at least 90% identical, such as at least 91%, 92%, 93%, 94%, 95%, 96%, 97%, 98%, 99%, or even 100% identical, to the nucleic acid sequence set forth as TGCCTCTGGCTTTGCAGTTA (SEQ ID NO: 10) or CACACAGGCACAGCAGAAACA (SEQ ID NO: 11). In several embodiments, a primer capable of hybridizing to and directing the amplification of a *Legionella pneumophila* serogroup 1 wzm nucleic acid molecule consists essentially of, or consists of a nucleic acid sequence set forth as SEQ ID NO: 10 or SEQ ID NO: 11. In particular embodiments, the primer capable of hybridizing to and directing amplification of a *Legionella pneumophila* serogroup 1 wzm nucleic acid molecule is capable of hybridizing to a wzm nucleic acid molecule from *Legionella pneumophila* serogroup 1, but not a wzm nucleic acid molecule from other *Legionella pneumophila* serogroups (for example, *Legionella pneumophila* serogroups Sg2, Sg3, Sg4, Sg5, Sg6, Sg7, Sg8, Sg9, Sg10, Sg11, Sg12, Sg13, or Sg14).

In several embodiments, a primer capable of hybridizing to and directing the amplification of a *Legionella bozemanii* gyrB nucleic acid molecule includes a nucleic acid sequence that is at least 90% identical, such as at least 91%, 92%, 93%, 94%, 95%, 96%, 97%, 98%, 99%, or even 100% identical, to the nucleic acid sequence set forth as TCCGCTGCTGAAGTGATTATG (SEQ ID NO: 18) or CATGCAAACCACCCGATACT (SEQ ID NO: 19). In several embodiments, a primer capable of hybridizing to and directing the amplification of a *Legionella bozemanii* gyrB nucleic acid molecule consists essentially of, or consists of a nucleic acid sequence set forth as SEQ ID NO: 18 or SEQ ID NO: 19. In particular embodiments, the primer capable of hybridizing to and directing amplification of a *Legionella bozemanii* gyrB nucleic acid molecule is also capable of hybridizing to and directing amplification of a gyrB nucleic acid molecule from *Legionella anisa, Legionella parisiensis*, and/or *Legionella tucsonensis.*

In several embodiments, a primer capable of hybridizing to and directing the amplification of a *Legionella dumoffii* legS2 nucleic acid molecule includes a nucleic acid sequence that is at least 90% identical, such as at least 91%, 92%, 93%, 94%, 95%, 96%, 97%, 98%, 99%, or even 100% identical, to the nucleic acid sequence set forth as CAGGAAAGCGCGACATCTAT (SEQ ID NO: 21) or ATCCAGCTCGTTCGCAATAA (SEQ ID NO: 22). In several embodiments, a primer capable of hybridizing to and directing the amplification of a *Legionella dumoffii* legS2 nucleic acid molecule consists essentially of, or consists of a nucleic acid sequence set forth as SEQ ID NO: 21 or SEQ ID NO: 22.

In several embodiments, a primer capable of hybridizing to and directing the amplification of a *Legionella feeleii* figA nucleic acid molecule includes a nucleic acid sequence that is at least 90% identical, such as at least 91%, 92%, 93%, 94%, 95%, 96%, 97%, 98%, 99%, or even 100% identical, to the nucleic acid sequence set forth as AACCGGTTTATCG-GTCTTT (SEQ ID NO: 24) or ATCAACCAGCTTGTCTCG (SEQ ID NO: 25). In several embodiments, a primer capable of hybridizing to and directing the amplification of a *Legionella feeleii* figA nucleic acid molecule consists essentially of, or consists of a nucleic acid sequence set forth as SEQ ID NO: 24 or SEQ ID NO: 25.

In several embodiments, a primer capable of hybridizing to and directing the amplification of a *Legionella longbeachae* ligB nucleic acid molecule includes a nucleic acid sequence that is at least 90% identical, such as at least 91%, 92%, 93%, 94%, 95%, 96%, 97%, 98%, 99%, or even 100% identical, to the nucleic acid sequence set forth as CTGCAGAAGT-TGCTGATTGTG (SEQ ID NO: 27) or GACGTGGCGAAT-GACTTATCT (SEQ ID NO: 28). In several embodiments, a primer capable of hybridizing to and directing the amplification of a *Legionella longbeachae* ligB nucleic acid molecule consists essentially of, or consists of a nucleic acid sequence set forth as SEQ ID NO: 27 or SEQ ID NO: 28. In particular embodiments, the primer capable of hybridizing to and directing amplification of a *Legionella longbeachae* ligB nucleic acid molecule is also capable of hybridizing to and directing amplification of a ligB nucleic acid molecule from *Legionella sainthelensis.*

In several embodiments, a primer capable of hybridizing to and directing the amplification of a *Legionella micdadei* migB nucleic acid molecule includes a nucleic acid sequence that is at least 90% identical, such as at least 91%, 92%, 93%, 94%, 95%, 96%, 97%, 98%, 99%, or even 100% identical, to the nucleic acid sequence set forth as TGACAAGTGAGAG-CAAGAGTT (SEQ ID NO: 30) or GTATCTATTCCGA-CAGCGATAGG (SEQ ID NO: 31). In several embodiments, a primer capable of hybridizing to and directing the amplification of a *Legionella micdadei* migB nucleic acid molecule consists essentially of, or consists of a nucleic acid sequence set forth as SEQ ID NO: 30 or SEQ ID NO: 31.

In certain embodiments, the primers are a set of primers, such as a pair of primers, capable of hybridizing to and amplifying a *Legionella* spp. ssrA nucleic acid molecule, a *Legionella pneumophila* mip nucleic acid molecule, a *Legionella pneumophila* serogroup 1 wzm nucleic acid molecule, a *Legionella bozemanii* gyrB nucleic acid molecule, a *Legionella dumoffii* legS2 nucleic acid molecule, a *Legionella feeleii* figA nucleic acid molecule, or a *Legionella micdadei* nucleic acid molecule. Such a set of primers includes at least one forward primer and a least one reverse primer, where the primers are specific for the amplification of a *Legionella* spp. ssrA nucleic acid molecule, a *Legionella pneumophila* mip nucleic acid molecule, a *Legionella pneumophila* serogroup 1 wzm nucleic acid molecule, a *Legionella bozemanii* gyrB nucleic acid molecule, a *Legionella dumoffii* legS2 nucleic acid molecule, a *Legionella feeleii* figA nucleic acid molecule, or a *Legionella micdadei* nucleic acid molecule.

In some examples, the set of primers includes a pair of primers that is specific for the amplification of a *Legionella* spp. nucleic acid molecule that includes a portion of the nucleic acid sequence of the *Legionella* spp. ssrA gene, such as the nucleic acid sequence set forth as SEQ ID NO: 2. In certain examples, the pair of primers includes a forward primer at least 90% identical to SEQ ID NO: 4, such as at least 91%, 92%, 93%, 94%, 95%, 96%, 97%, 98%, 99%, or 100% identical to SEQ ID NO: 4, and a reverse primer at least 90% identical to SEQ ID NO: 5, such as at least 91%, 92%, 93%, 94%, 95%, 96%, 97%, 98%, 99%, or 100% identical to SEQ ID NO: 5.

In some examples, the set of primers includes a pair of primers that is specific for the amplification of a *Legionella pneumophila* nucleic acid molecule that includes a portion of the nucleic acid sequence of the *Legionella pneumophila* mip gene, such as the nucleic acid sequence set forth as SEQ ID NO: 1. In certain examples, the pair of primers includes a forward primer at least 90% identical to SEQ ID NO: 7, such as at least 91%, 92%, 93%, 94%, 95%, 96%, 97%, 98%, 99%, or 100% identical to SEQ ID NO: 7, and a reverse primer at least 90% identical to SEQ ID NO: 8, such as at least 91%, 92%, 93%, 94%, 95%, 96%, 97%, 98%, 99%, or 100% identical to SEQ ID NO: 8.

In some examples, the set of primers includes a pair of primers that is specific for the amplification of a *Legionella pneumophila* serogroup 1 nucleic acid molecule that includes a portion of the nucleic acid sequence of the *Legionella pneumophila serogroup* 1 wzm gene, such as the nucleic acid sequence set forth as SEQ ID NO: 3. In certain examples, the pair of primers includes a forward primer at least 90% identical to SEQ ID NO: 10, such as at least 91%, 92%, 93%, 94%, 95%, 96%, 97%, 98%, 99%, or 100% identical to SEQ ID NO: 10, and a reverse primer at least 90% identical to SEQ ID NO: 11, such as at least 91%, 92%, 93%, 94%, 95%, 96%, 97%, 98%, 99%, or 100% identical to SEQ ID NO: 11.

In some examples, the set of primers includes a pair of primers that is specific for the amplification of a *Legionella bozemanii* nucleic acid molecule that includes a portion of the nucleic acid sequence of the *Legionella bozemanii* gyrB gene, such as the nucleic acid sequence set forth as SEQ ID NO: 13. In certain examples, the pair of primers includes a forward primer at least 90% identical to SEQ ID NO: 18, such as at least 91%, 92%, 93%, 94%, 95%, 96%, 97%, 98%, 99%, or 100% identical to SEQ ID NO: 18, and a reverse primer at least 90% identical to SEQ ID NO: 19, such as at least 91%, 92%, 93%, 94%, 95%, 96%, 97%, 98%, 99%, or 100% identical to SEQ ID NO: 19.

In some examples, the set of primers includes a pair of primers that is specific for the amplification of a *Legionella dumoffii* nucleic acid molecule that includes a portion of the nucleic acid sequence of the *Legionella dumoffii* legS2 gene, such as the nucleic acid sequence set forth as SEQ ID NO: 14. In certain examples, the pair of primers includes a forward primer at least 90% identical to SEQ ID NO: 21, such as at least 91%, 92%, 93%, 94%, 95%, 96%, 97%, 98%, 99%, or 100% identical to SEQ ID NO: 21, and a reverse primer at least 90% identical to SEQ ID NO: 22, such as at least 91%, 92%, 93%, 94%, 95%, 96%, 97%, 98%, 99%, or 100% identical to SEQ ID NO: 22.

In some examples, the set of primers includes a pair of primers that is specific for the amplification of a *Legionella feeleii* nucleic acid molecule that includes a portion of the nucleic acid sequence of the *Legionella feeleii* figA gene, such as the nucleic acid sequence set forth as SEQ ID NO: 15. In certain examples, the pair of primers includes a forward primer at least 90% identical to SEQ ID NO: 24, such as at least 91%, 92%, 93%, 94%, 95%, 96%, 97%, 98%, 99%, or 100% identical to SEQ ID NO: 24, and a reverse primer at least 90% identical to SEQ ID NO: 25, such as at least 91%, 92%, 93%, 94%, 95%, 96%, 97%, 98%, 99%, or 100% identical to SEQ ID NO: 25.

In some examples, the set of primers includes a pair of primers that is specific for the amplification of a *Legionella longbeachae* nucleic acid molecule that includes a portion of the nucleic acid sequence of the *Legionella longbeachae* ligB gene, such as the nucleic acid sequence set forth as SEQ ID NO: 16. In certain examples, the pair of primers includes a forward primer at least 90% identical to SEQ ID NO: 27, such as at least 91%, 92%, 93%, 94%, 95%, 96%, 97%, 98%, 99%, or 100% identical to SEQ ID NO: 27, and a reverse primer at least 90% identical to SEQ ID NO: 28, such as at least 91%, 92%, 93%, 94%, 95%, 96%, 97%, 98%, 99%, or 100% identical to SEQ ID NO: 28.

In some examples, the set of primers includes a pair of primers that is specific for the amplification of a *Legionella micdadei* nucleic acid molecule that includes a portion of the nucleic acid sequence of the *Legionella micdadei* migB gene, such as the nucleic acid sequence set forth as SEQ ID NO: 17. In certain examples, the pair of primers includes a forward primer at least 90% identical to SEQ ID NO: 30, such as at least 91%, 92%, 93%, 94%, 95%, 96%, 97%, 98%, 99%, or 100% identical to SEQ ID NO: 30, and a reverse primer at least 90% identical to SEQ ID NO: 31, such as at least 91%, 92%, 93%, 94%, 95%, 96%, 97%, 98%, 99%, or 100% identical to SEQ ID NO: 31.

Although exemplary probe and primer sequences are provided in SEQ ID NOs: 4-12 and 18-36, the primer and/or probe sequences can be varied slightly by moving the probe or primer a few nucleotides upstream or downstream from the nucleotide positions that they hybridize to on the target nucleic molecule acid, provided that the probe and/or primer is still specific for the target nucleic acid sequence, for example specific for one of SEQ ID NOs: 1-3 and 13-17. For example, variations of the probes and primers disclosed as SEQ ID NOs: 4-12 and 18-36 can be made by "sliding" the probes and/or primers a few nucleotides 5' or 3' from their positions, and such variation will still be specific for the respective target nucleic acid sequence.

Also provided by the present disclosure are probes and primers that include variations to the nucleotide sequences shown in any of SEQ ID NOs: 4-12 and 18-36, as long as such variations permit detection of the target nucleic acid molecule. For example, a probe or primer can have at least 90% sequence identity such as at least 91%, 92%, 93%, 94%, 95%, 96%, 97%, 98%, or 99% identity to a nucleic acid consisting of the sequence shown in any of SEQ ID NOs: 4-12 and 18-36. In such examples, the number of nucleotides does not change, but the nucleic acid sequence shown in any of SEQ ID NOs: 4-12 and 18-36 can vary at a few nucleotides, such as changes at 1, 2, 3, or 4 nucleotides.

The present application also provides probes and primers that are slightly longer or shorter than the nucleotide sequences shown in any of SEQ ID NOs: 4-12 and 18-36, as long as such deletions or additions permit detection of the desired target nucleic acid molecule. For example, a probe or primer can include a few nucleotide deletions or additions at the 5'- or 3'-end of the probe or primers shown in any of SEQ ID NOs: 4-12 and 18-36, such as addition or deletion of 1, 2, 3, or 4 nucleotides from the 5'- or 3'-end, or combinations thereof (such as a deletion from one end and an addition to the other end). In such examples, the number of nucleotides changes.

Also provided are probes and primers that are degenerate at one or more positions (such as 1, 2, 3, 4, 5, or more positions), for example, a probe or primer that includes a mixture of nucleotides (such as 2, 3, or 4 nucleotides) at a specified position in the probe or primer. In some examples, the probes and primers disclosed herein include one or more synthetic bases or alternative bases (such as inosine). In other examples, the probes and primers disclosed herein include one or more modified nucleotides or nucleic acid analogues, such as one or more locked nucleic acids (see, e.g., U.S. Pat. No. 6,794,499) or one or more superbases (Nanogen, Inc., Bothell, Wash.). In other examples, the probes and primers disclosed herein include a minor groove binder conjugated to the 5' or 3' end of the oligonucleotide (see, e.g., U.S. Pat. No. 6,486,308).

V. Kits

The nucleic acid primers and probes disclosed herein can be supplied in the form of a kit for use in the detection and/or discrimination of *Legionella* spp., *Legionella pneumophila*, and/or *Legionella pneumophila* serogroup 1 in a sample. In such a kit, an appropriate amount of one or more (such as 2, 3, 4, 5, 6, 7, 8, or more) of the nucleic acid probes and/or primers (such probes and primers as disclosed herein, for example SEQ ID NOs: 4-12 and 18-36) are provided in one or more containers. A nucleic acid probe and/or primer may be provided suspended in an aqueous solution or as a freeze-dried or lyophilized powder, for instance. The container(s) in which the nucleic acid(s) are supplied can be any conventional container that is capable of holding the supplied form, for instance, microfuge tubes, ampoules, or bottles. The kits can include either labeled or unlabeled nucleic acid probes for use in detection of *Legionella* nucleic acids. One or more control probes and/or primers for use in the PCR reactions also may be supplied in the kit (for example, for the detection of human RNase P). In some examples, the probes are detectably labeled. The kit may also include one or more positive controls such as a synthetic positive control (such as a combined positive control).

In some examples, one or more sets of primers (such as the primers described above), such as pairs of primers (for example, one pair, two pairs, three pairs, four pairs, five pairs, six pairs, seven pairs, eight pairs, or more of primers), may be provided in pre-measured single use amounts in individual, typically disposable, tubes or equivalent containers. With such an arrangement, the sample to be tested for the presence of the target nucleic acids can be added to the individual tube(s) and amplification carried out directly.

The amount of nucleic acid primer supplied in the kit can be any appropriate amount, and may depend on the target market to which the product is directed. For instance, if the kit is adapted for research or clinical use, the amount of each nucleic acid primer provided would likely be an amount sufficient to prime several PCR amplification reactions. General guidelines for determining appropriate amounts may be found in Innis et al., Sambrook et al., and Ausubel et al.

In some embodiments, kits also may include one or more additional reagents necessary to carry out PCR amplification reactions, including DNA sample preparation reagents, appropriate buffers (such as polymerase buffer), salts (for example, magnesium chloride), deoxyribonucleotides (dNTPs), and polymerases.

In particular embodiments, the kit includes prepackaged probes, such as probes suspended in suitable medium in individual containers (for example, individually sealed tubes). In some examples, the probes include those provided herein. In other particular embodiments, the kit includes equipment, reagents, and instructions for extracting and/or purifying nucleotides from a sample.

The present disclosure is illustrated by the following non-limiting Examples.

EXAMPLE 1

Primers and Probes

Primers and probes were designed for detection of *Legionella* spp. (Pan-Leg), *Legionella pneumophila* (Lp), *L.*

*pneumophila* Sg1 (Lp1), *Legionella bozemanii, Legionella dumoffii, Legionella feeleii, Legionella longbeachae* (LLB), and *Legionella micdadei*. The target genes and primer and probe sequences are shown in Table 1.

TABLE 1

Primers and probes for detection of *Legionella*

| Primer/Probe ID | Sequence (5'-3') | Target | SEQ ID NO: |
|---|---|---|---|
| *Legionella* spp. | | | |
| PanLeg-F | GGCGACCTGGCTTC | ssrA | 4 |
| PanLeg-R | GGTCATCGTTTGCATTTATATTTA | | 5 |
| PanLeg-P1 | CGTGGGTTGCAA | | 6 |
| *Legionella pneumophila* | | | |
| Lp-F | TTGTCTTATAGCATTGGTGCCG | mip | 7 |
| Lp-R | CCAATTGAGCGCCACTCATAG | | 8 |
| Lp-P | CGGAAGCAATGGCTAAAGGCATGCA | | 9 |
| *Legionella pneumophila* serogroup 1 | | | |
| Lp1-F | TGCCTCTGGCTTTGCAGTTA | wzm | 10 |
| Lp1-R | CACACAGGCACAGCAGAAACA | | 11 |
| Lp1-P | TTTATTACTCCACTCCAGCGAT | | 12 |
| *Legionella bozemanii* | | | |
| bozemanii-F | TCCGCTGCTGAAGTGATTATG | gyrB | 18 |
| bozemanii-R | CATGCAAACCACCCGATACT | | 19 |
| bozemanii-P | GTGCTTCACGCCGGTGGTAAATTT | | 20 |
| bozemanii-P2 | TGCTTCACGCCGGTGGTAAATTTG | | 33 |
| bozemanii-P3 | AAATTTACCACCGGCGTGAAGCAC | | 35 |
| *Legionella dumoffii* | | | |
| dumoffii-F | CAGGAAAGCGCGACATCTAT | legS2 | 21 |
| dumoffii-R | ATCCAGCTCGTTCGCAATAA | | 22 |
| dumoffii-P | TGGAAACCCTCAATGGTCCGTTCT | | 23 |
| *Legionella feeleii* | | | |
| feeleii-F | AACCGGTTTATCGGTCTTT | figA | 24 |
| feeleii-R | ATCAACCAGCTTGTCTCG | | 25 |
| feeleii-P | GCGAGTGATAATCCATCAAATTCTC AAGCT | | 26 |
| feeleii-P1 | AGCGAGTGATAATCCATCAAATTCT CAAGC | | 34 |
| feeleii-P2 | AGCTTGAGAATTTGATGGATTATCA CTCGC | | 36 |
| *Legionella longbeachae* | | | |
| LLB-F1 | CTGCAGAAGTTGCTGATTGTG | ligB | 27 |
| LLB-R1 | GACGTGGCGAATGACTTATCT | | 28 |
| LLB-P1 | TGTCGCCAAGAAGTTGTATCTCATG CT | | 29 |
| *Legionella micdadei* | | | |
| micdadei-F | TGACAAGTGAGAGCAAGAGTT | migB | 30 |
| micdadei-R | GTATCTATTCCGACAGCGATAGG | | 31 |
| micdadei-P | ACAGAAGGAGAACCTTCCGGTGTG | | 32 |

For multiplex PCR, probes were labeled as follows: *Legionella* spp. PanLeg-P1 (SEQ ID NO: 6), 5'-FAM and 3'-MGBNFQ; *Legionella pneumophila* Lp-P (SEQ ID NO: 9), 5'-Quasar 670 and 3'-BHQ3; *Legionella pneumophila* serogroup 1 Lp1-P (SEQ ID NO: 12), 5'-VIC and 3'-MGB-NFQ; *Legionella bozemanii* bozemanii-P, bozemanii-P2, and bozemanii-P3 (SEQ ID NOs: 20, 33, and 35, respectively), 5"-Quasar705 and 3'-BHQ3; *Legionella dumoffii* dumoffii-P (SEQ ID NO: 23), 5'-HEX and 3"-BHQ1; *Legionella feeleii* feeleii-P, feeleii-P1, and feeleii-P2 (SEQ ID NOs: 26, 34, and 36, respectively), 5"-TexasRed 615 and 3"-BHQ2; *Legionella longbeachae* LLB-P (SEQ ID NO: 29), 5"-Quasar670 and 3"-BHQ3; *Legionella micdadei* micdadei-P, 5"-FAM and 3"-BHQ1.

EXAMPLE 2

*Legionella pneumophila* Real-Time PCR Assays

Primers and probes were initially tested for each organism in real-time singleplex PCR. For the multiplex assay, all primers and probes were pooled in a single tube reaction. Probes were labeled as described in Example 1. Primers were used at a final concentration of 500 nM each and probes were used at a final concentration of 100 nM each for both singleplex and multiplex assays.

Purified total nucleic acid from *Legionella pneumophila* strain Philadelphia was used as a positive control. The multiplex reaction contained 12.5 μl PerfeCTa™ Multiplex qPCR SuperMix (Quanta Biosciences, Gaithersburg, Md.), 0.5 μl of each primer and probe, 3 μl of nuclease-free water and 5 μl template, to a final volume of 25 μl. The assay was performed on the ABI 7500 Real-Time PCR system with the following thermocycling conditions: 95° C. for 5 minutes followed by 45 cycles of 95° C. for 15 seconds and 60° C. for 1 minute.

Culture positive and negative respiratory clinical specimens and water samples were collected and processed during domestic outbreaks and acquired by the Centers for Disease Control. Total nucleic acid from 200 μl of clinical specimen was extracted using the MagNA Pure Compact and eluted in 100 μl. Total nucleic acid from 1 ml of processed water sample (post-concentration/filtration) was extracted using the MagNA Pure LC and eluted in 50 μl.

Analytical sensitivity was determined by testing in replicates of 10, a serial dilution (10-fold) series of *L. pneumophila* strain Philadelphia nucleic acid. Limits of detection were established for each assay and defined as the lowest dilution in which >50% of replicates had positive Ct values.

Analytical specificity for each assay was verified using a comprehensive panel of 44 non-*Legionella* samples. The panel included: *B. pertussis, C. albicans, C. pneumoniae, C. trachomatis, C. psittaci, C. diphtheriae, E. coli, H. influenzae* Type b, *K. pneumoniae, L. planetarium, M. pneumoniae, M. genitalium, M. pirum, M. salivarum, M. hominis, M. orale, M. buccale, M. facium, M. lipophilum, M. catarrhalis, M. tuberculosis, N. meningitidis, P. aeruginosa, S. aureus, S. agalactiae, S. pneumoniae, S. pyogenes, T. gondii, U. urealyticum*, human DNA, human coronavirus, human rhinovirus, human parainfluenza virus 1, human parainfluenza virus 2, human parainfluenza virus 3, human parainfluenza virus 4, human adenovirus, influenza virus A, influenza virus B, human respiratory syncytial virus, human rubella virus, human parechovirus, human metapneumovirus and human enterovirus. No cross-reactivity or non-specific amplification was observed for any of the assays tested with these organisms.

Figure 1B:
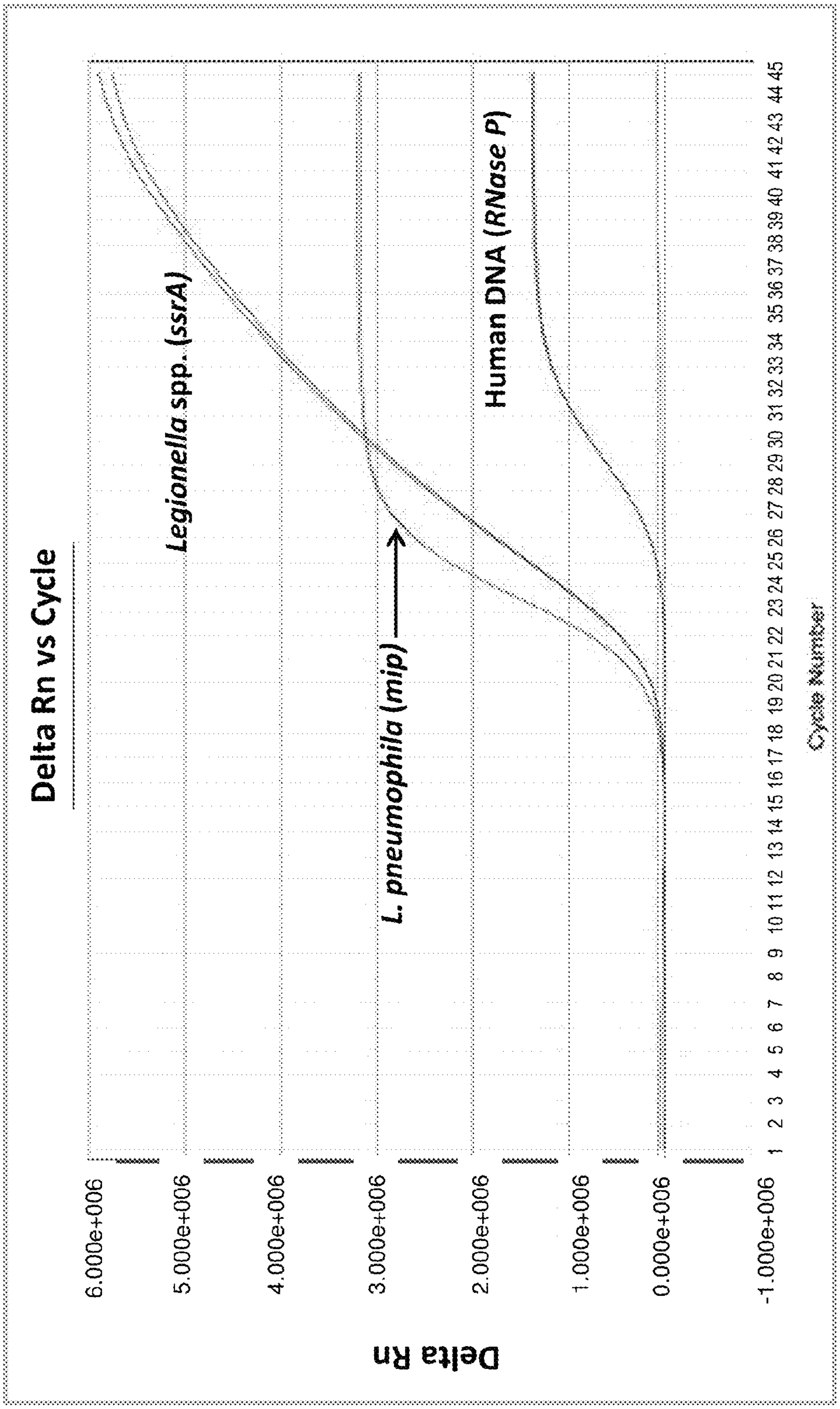
FIG. 1B is a graph showing results from multiplex real-time PCR in a sample containing *Legionella pneumophila* serogroup 2 DNA and human DNA.
Figure 1C:
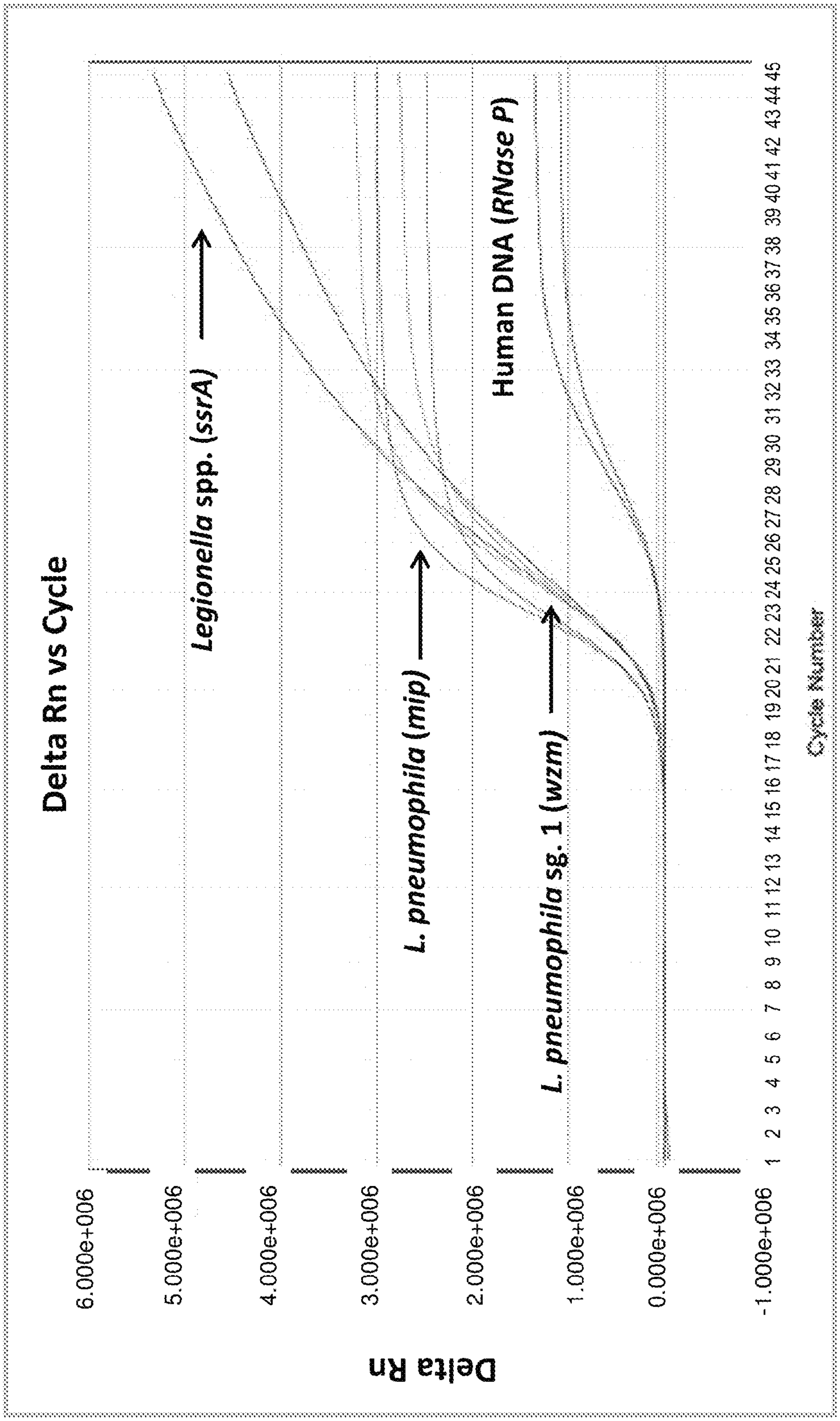
FIG. 1C is a graph showing results from multiplex real-time PCR in a sample containing *Legionella pneumophila* serogroup 1 DNA and human DNA.

The multiplex assay was capable of simultaneously detecting and discriminating *Legionella* spp., *Legionella pneumophila*, and *Legionella pneumophila* serogroup 1 (FIGS. 1A-C). Evaluation of the multiplex assay with 215 *Legionella* species strains (Table 2) and 44 non-*Legionella* strains demonstrated 100% specificity. The assay showed a 7-log dynamic range displaying an analytical sensitivity of 25 fg for each target per reaction in both the singleplex and multiplex assays. Further evaluation with culture-positive clinical and environmental samples demonstrated sensitivity rates of 100% and 80%, respectively (Table 3).

TABLE 2

Strains used for evaluating multiplex real-time PCR

| Strains | No. of strains tested |
|---|---|
| *L. pneumophila* serogroup 1 | 73 |
| *L. pneumophila* serogroup 2-17 | 73 |
| *L. adelaidensis* | 1 |
| *L. anisa* | 3 |
| *L. beliardensis* | 1 |
| *L. birminghamensis* | 2 |
| *L. bozemanii* | 2 |
| *L. brunensis* | 1 |
| *L. busanensis* | 1 |
| *L. cherrii* | 1 |
| *L. cincinnatiensis* | 1 |
| *L. drozanskii* | 1 |
| *L. dumoffii* | 1 |
| *L. erythra* | 1 |
| *L. fairfieldensis* | 1 |
| *L. fallonii* | 1 |
| *L. feeleii* | 2 |
| *L. geestiana* | 1 |
| *L. genomo* species | 1 |
| *L. gormanii* | 1 |
| *L. gratiana* | 1 |
| *L. gresilensis* | 1 |
| *L. hackliae* | 2 |
| *L. impletisoli* | 1 |
| *L. israelensis* | 1 |
| *L. jamestowniensis* | 1 |
| *L. jordanis* | 1 |
| *L. lansingensis* | 1 |
| *L. longbeachae* | 3 |
| *L. londoniensis* | 1 |
| *L. lytica* | 1 |
| *L. maceachernii* | 1 |
| *L. micdadei* | 1 |
| *L. moravica* | 1 |
| *L. nagasakiensis* | 2 |
| *L. nautarum* | 1 |
| *L. oakridgensis* | 2 |
| *L. parisiensis* | 1 |
| *L. quateirensis* | 1 |
| *L. quinlavanii* | 2 |
| *L. rowbowthamii* | 1 |
| *L. rubriluscens* | 1 |
| *L. sainthelensis* | 2 |
| *L. santicrucis* | 1 |
| *L. shakespearei* | 1 |
| *L. spiritensis* | 2 |
| *L. steigerwaltii* | 1 |
| *L. taurinensis* | 1 |
| *L. tucsonensis* | 3 |
| *L. wadsworthii* | 1 |
| *L. waltersii* | 1 |
| *L. worsleiensis* | 1 |
| *L. yabuchiae* | 1 |
| Unidentified *Legionella* (LLO) | 3 |

TABLE 3

Sensitivity of pathogen detection in clinical and water samples

| | | | | Multiplex real-time PCR Ct values | | | |
|---|---|---|---|---|---|---|---|
| Sample # | Source | Culture | Serology | *Legionella* spp. (ssrA) | *L. pneumophila* (mip) | *L. pneumophila* sg. 1 (wzm) | Human DNA (RNase P) |
| 1 | Sputum | Positive | Lp sg. 1 | 27.63 | 26.84 | 27.74 | 25.96 |
| 2 | Lung | Positive | Lp sg. 1 | 17.15 | 16.85 | 17.11 | 17.66 |
| 3 | Lung | Positive | Lp sg. 1 | 15.14 | 14.97 | 15.19 | 16.56 |
| 4 | Br. swab | Positive | Lp sg. 1 | 25.53 | 24.47 | 24.53 | 23.91 |
| 5 | Lung | Positive | Lp sg. 1 | 26.89 | 26.18 | 25.95 | 20.00 |
| 6 | Lung | Positive | Lp sg. 1 | 28.55 | 28.07 | 26.98 | 17.66 |
| 7 | Lung | Positive | Lp sg. 1 | 25.19 | 24.37 | 24.17 | 19.59 |
| 8 | Lung | Positive | Lp sg. 1 | 25.93 | 25.30 | 24.72 | 19.05 |
| 9 | Lung | Positive | Lp sg. 1 | 29.36 | 28.74 | 28.27 | 20.50 |
| 10 | Lung | Positive | Lp sg. 1 | 26.04 | 25.18 | 25.15 | 17.50 |
| 11 | Lung | Positive | Lp sg. 1 | 26.54 | 25.97 | 25.81 | 21.24 |
| 12 | Lung | Positive | Lp sg. 1 | 26.72 | 27.07 | 26.52 | 19.83 |
| 13 | BAL | Positive | Lp sg. 1 | 33.17 | 32.13 | 31.97 | 24.70 |
| 14 | Sputum | Positive | Lp sg. 1 | 27.88 | 27.21 | 26.66 | 16.75 |
| 15 | Lung | Positive | Lp sg. 1 | 28.18 | 27.24 | 26.95 | 20.48 |
| 16 | OP swab | Negative | — | Undet. | Undet. | Undet. | 24.11 |
| 17 | Urine | Negative | — | Undet. | Undet. | Undet. | 23.07 |
| 18 | OP swab | Negative | — | Undet. | Undet. | Undet. | 25.17 |
| 19 | NP swab | Negative | — | Undet. | Undet. | Undet. | 24.56 |
| 20 | Sputum | Negative | — | Undet. | Undet. | Undet. | 22.26 |
| 21 | Sputum | Negative | — | Undet. | Undet. | Undet. | 23.98 |
| 19 | Water | Positive | mixed | 25.94 | Undet. | 37.31 (⅔) | N/T |
| 20 | Water | Positive | Lp sg. 1 | 33.00 | Undet. | 38.11 | N/T |
| 21 | Water | Positive | Lp sg. 1 | 34.58 (⅔) | 34.78 | 35.44 (⅔) | N/T |
| 22 | Water | Positive | Lp | 29.85 | Undet. | Undet. | N/T |
| 23 | Water | Positive | Leg. spp. | Undet. | Undet. | Undet. | N/T |
| 24 | Water | Positive | Leg. spp. | Undet. | Undet. | Undet. | N/T |
| 25 | Water | Positive | mixed | 29.33 | 28.65 | 38.35 | N/T |
| 26 | Water | Positive | Leg. spp. | 32.19 | 33.37 | 33.60 (⅔) | N/T |
| 27 | Water | Positive | Lp | Undet. | Undet. | Undet. | N/T |
| 28 | Water | Positive | mixed | 32.71 | 34.93 | 35.61 | N/T |
| 29 | Water | Positive | Lp | Undet. | Undet. | Undet. | N/T |
| 30 | Water | Positive | Lp | 29.05 | Undet. | Undet. | N/T |
| 31 | Water | Positive | Lp sg. 1 | Undet. | 33.94 (⅓) | 35.70 (⅓) | N/T |
| 32 | Water | Positive | mixed | 34.52 (⅔) | 34.15 | 39.57 (⅔) | N/T |
| 33 | Water | Positive | Lp sg. 1 | 40.05 (⅓) | Undet. | Undet. | N/T |

TABLE 3-continued

Sensitivity of pathogen detection in clinical and water samples

| Sample # | Source | Culture | Serology | Multiplex real-time PCR Ct values: *Legionella* spp. (ssrA) | *L. pneumophila* (mip) | *L. pneumophila* sg. 1 (wzm) | Human DNA (RNase P) |
|---|---|---|---|---|---|---|---|
| 34 | Water | Positive | Leg. spp. | Undet. | Undet. | 32.03 | N/T |
| 35 | Water | Negative | — | Undet. | Undet. | Undet. | N/T |
| 36 | Water | Negative | — | 37.69 (⅓) | Undet. | 34.79 (⅔) | N/T |
| 37 | Water | Negative | — | 31.14 | 34.14 (⅔) | 35.64 (⅓) | N/T |
| 38 | Water | Negative | — | Undet. | Undet. | Undet. | N/T |

EXAMPLE 3

Non-*Legionella pneumophila* Species Real-Time PCR Assays

Primers and probes were initially tested for each non-pneumophila species in real-time singleplex PCR. For the multiplex assay, all primers and probes were pooled in a single tube reaction. Probes bozemanii-P, dumoffii-P, feeleii-P, LLB-P1, and micdadei-P were used and were labeled as described in Example 1. Total nucleic acid from *Legionella* typing strains, clinical and/or environmental isolates was extracted with the MagNA Pure LC instrument (Roche Applied Bioscience, Indianapolis, Ind.) using the Total Nucleic Acid Isolation Kit following manufacturer's instructions and nucleic acid concentration was normalized to 1 ng/μl. The multiplex reaction contained 12.5 μl PerfeCTa™ Multiplex qPCR SuperMix (Quanta Biosciences, Gaithersburg, Md.), 0.5 μl of each primer and probe, and 5 μl of template, to a final volume of 25 μl Primers/probe final concentrations were 250 nM/50 nm, respectively. The assay was performed on the Rotor-Gene 6000 system (Qiagen, USA) under the following conditions: 95° C. for 5 minutes followed by 45 cycles of 95° C. for 15 seconds and 60° C. for 1 minute.

Figure 2A:
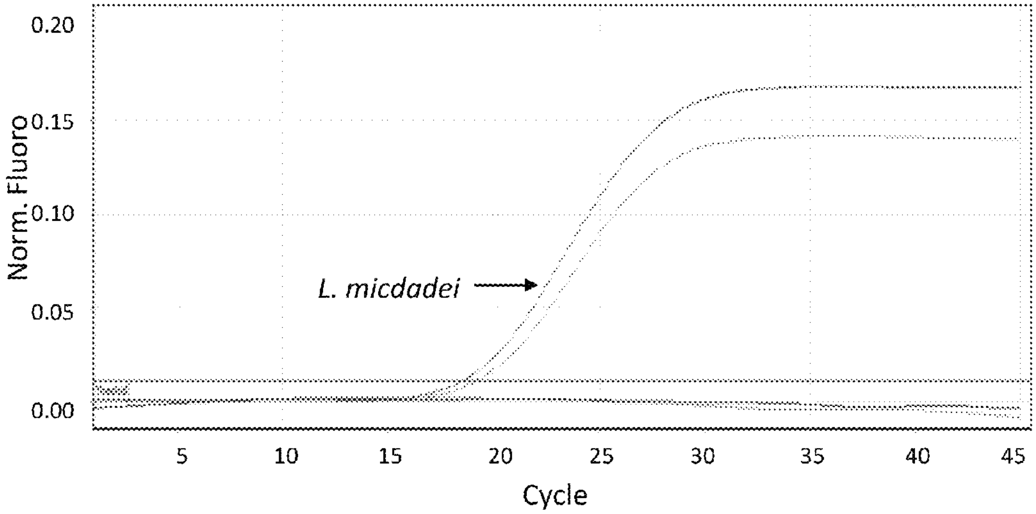
FIGS. 2A-E are a series of graphs showing results from multiplex real-time PCR for *Legionella micdadei*(A), *Legionella dumoffii* (B), *Legionella feeleii* (C), *Legionella longbeachae* and *Legionella sainthelensis* serogroup 1 (sg1) and serogroup 2 (sg2) (D), and *Legionella bozemanii, Legionella anisa, Legionella parisiensis* and *Legionella tucsonensis* serogroup 1 (sg1) and serogroup 3 (sg3) (E). All samples were run in duplicate. Nucleic acid was normalized to 1 ng/μl.
Figure 2B:
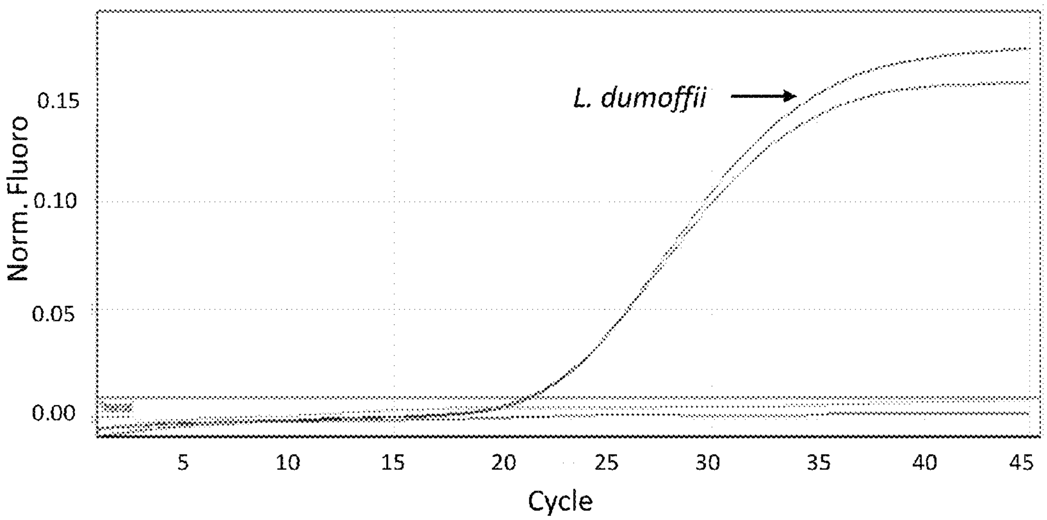
Figure 2C:
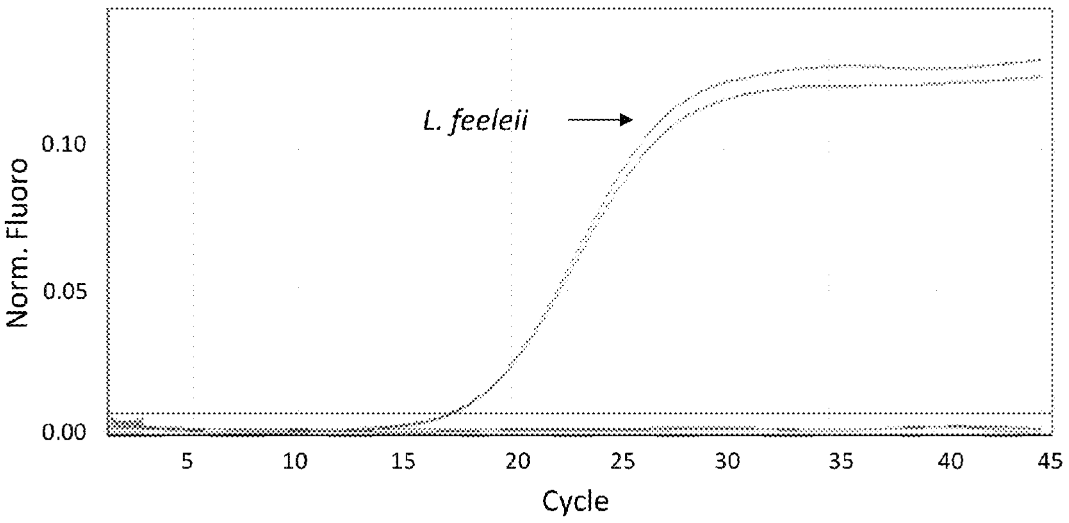
Figure 2D:
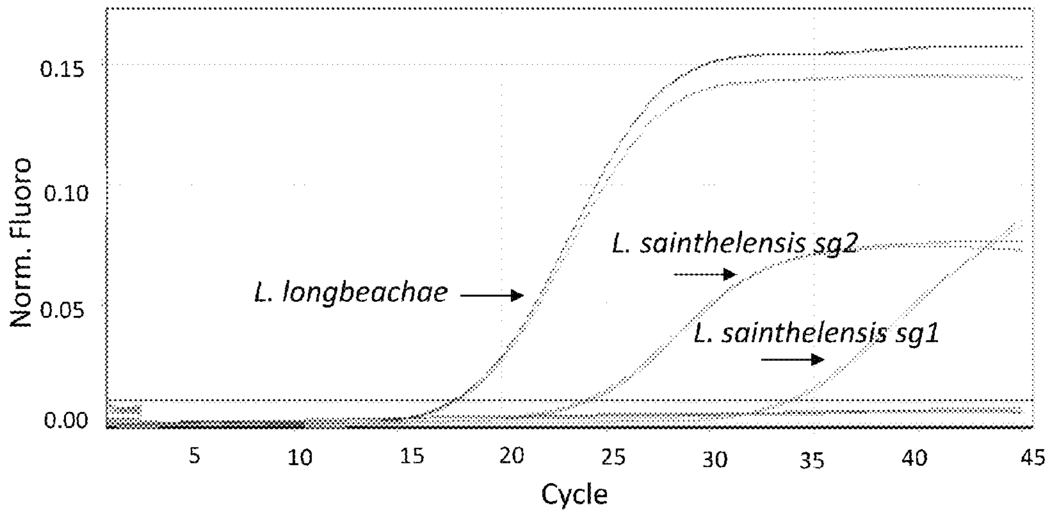
Figure 2E:
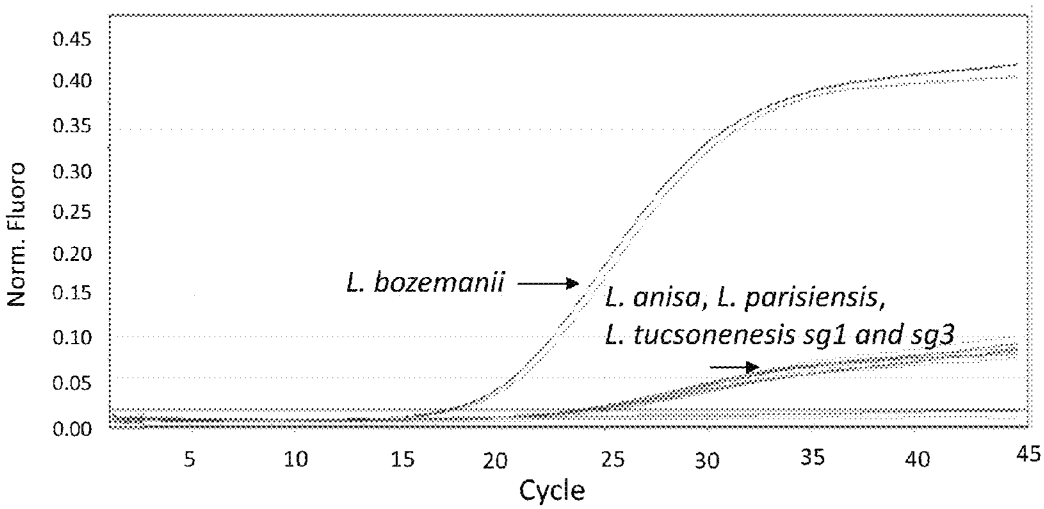
Figure 3:
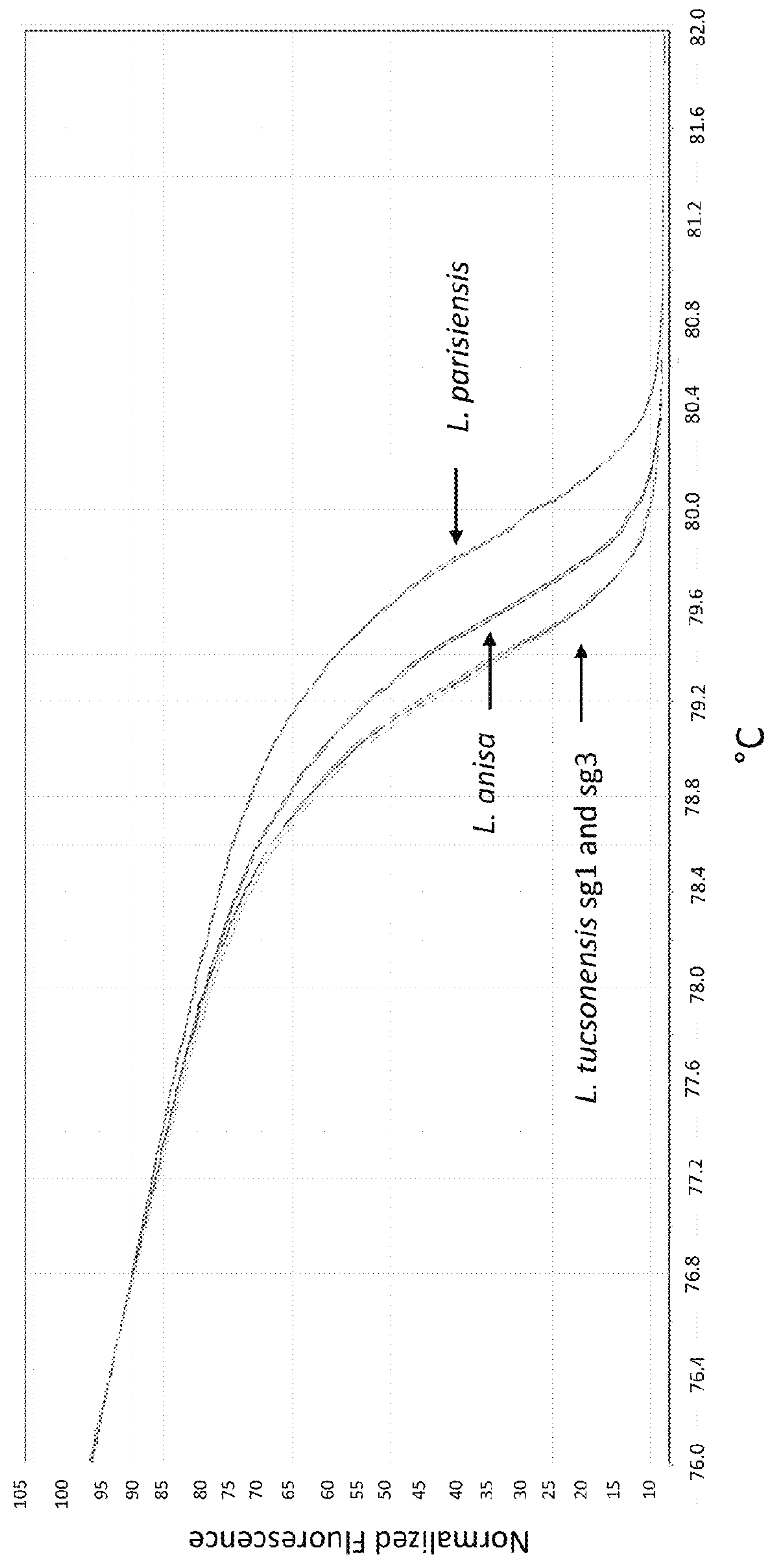
FIG. 3 is a graph showing tmRNA high-resolution melt analysis for discrimination of *Legionella anisa, Legionella parisiensis* and *Legionella tucsonensis* serogroup 1 (sg1) and serogroup 3 (sg3).

Evaluation of the assay with nucleic acid from 27 *L. bozemanii,* 21 *L. dumoffii,* 11 *L. feeleii,* 79 *L. longbeachae*, and 21 *L. micdadei* clinical and/or environmental isolates and typing strains demonstrated 100% sensitivity (FIG. 2A-E). Cross-reactivity of primers/probe for the *L. longbeachae* (Ct value 17-20) assay allowed for additional detection and discrimination of *L. sainthelensis* serogroup (sg) 1 (Ct value 32-35) and *L. sainthelensis* sg 2 (Ct value 24-27) based on Ct values (FIG. 2D). Cross-reactivity was also observed with the *L. bozemanii* (Ct value 17-20) assay, allowing for detection of three more *Legionella* species, *L. anisa, L. parisiensis* and *L. tucsonensis* sg1 and sg3 (Ct values 24-27) based on Ct value (FIG. 2E). These species could be further discriminated by performing a real-time PCR assay followed by high-resolution melt analysis targeting the tmRNA gene (FIG. 3).

In view of the many possible embodiments to which the principles of the disclosure may be applied, it should be recognized that the illustrated embodiments are only examples and should not be taken as limiting the scope of the invention. Rather, the scope of the invention is defined by the following claims. We therefore claim as our invention all that comes within the scope and spirit of these claims.

We claim:

1. A method for detecting presence of *Legionella* nucleic acid in a sample, comprising:

(i) simultaneously contacting the sample with:

a first probe consisting of the nucleic acid sequence of SEQ ID NO: 6 and a detectable label, a primer consisting of the nucleic acid sequence of SEQ ID NO: 4, and a primer consisting of the nucleic acid sequence of SEQ ID NO: 5;

a second probe consisting of the nucleic acid sequence of SEQ ID NO: 9 and a detectable label, a primer consisting of the nucleic acid sequence of SEQ ID NO: 7, and a primer consisting of the nucleic acid sequence of SEQ ID NO: 8; and a third probe consisting of the nucleic acid sequence of SEQ ID NO: 12 and a detectable label, a primer consisting of the nucleic acid sequence of SEQ ID NO: 10, and a primer consisting of the nucleic acid sequence of SEQ ID NO: 11;

(ii) amplifying a *Legionella* spp. ssrA nucleic acid, a *Legionella pneumophila* mip nucleic acid, and a *Legionella pneumophila* serogroup 1 wzm nucleic acid and (iii) detecting hybridization between one or more detectably labeled probe and a nucleic acid, wherein detection of hybridization between the first probe and a nucleic acid indicates presence of *Legionella* spp. in the sample, detection of hybridization between the second probe and a nucleic acid indicates presence of *Legionella pneumophila* in the sample, and detection of hybridization between the third probe and a nucleic acid indicates presence of *Legionella pneumophila* serogroup 1 in the sample.

2. The method of claim 1, wherein detecting hybridization comprises detecting a change in signal from one or more detectably labeled probe during or after hybridization relative to signal from the label before hybridization.

3. The method of claim 1, further comprising contacting the sample with one or more of:

a fourth probe consisting of the nucleic acid sequence of SEQ ID NO: 20 SEQ ID NO: 33, or SEQ ID NO: 35 and a detectable label;

a fifth probe consisting of the nucleic acid sequence of SEQ ID NO: 23 and a detectable label;

a sixth probe consisting of the nucleic acid sequence of SEQ ID NO: 26, SEQ ID NO: 34, or SEQ ID NO: 36 and a detectable label;

a seventh probe consisting of the nucleic acid sequence of SEQ ID NO: 29 and a detectable label; and an eighth probe consisting of the nucleic acid sequence of SEQ ID NO: 32 and a detectable label; and detecting hybridization between one or more detectably labeled probe and a nucleic acid, wherein detection of hybridization between the fourth probe and a nucleic acid indicates presence of *Legionella bozemanii* in the sample, detection of hybridization between the fifth probe and a nucleic acid indicates presence of *Legionella dumoffii* in the sample, detection of hybridization between the sixth probe and a nucleic acid indicates presence of *Legionella feeleii* in the sample, detection of hybridization between the seventh probe and a nucleic acid indicates presence of *Legionella longbeachae* in the sample, and detection of hybridization between the eighth probe and a nucleic acid indicates presence of *Legionella micdadei* in the sample.

4. The method of claim 3, further comprising amplifying one or more of a *Legionella bozemanii* gyrB nucleic acid, a *Legionella dumoffii* legS2 nucleic acid, a *Legionella feeleii* figA nucleic acid, a *Legionella longbeachae* ligB nucleic acid, or a *Legionella micdadei* migB nucleic acid prior to or simultaneously with contacting the sample with the fourth, fifth, sixth, seventh, and/or eighth probes, wherein:

amplifying the *Legionella bozemanii* gyrB nucleic acid comprises contacting the sample with a primer consisting of the nucleic acid sequence of SEQ ID NO: 18 and a primer consisting of the nucleic acid sequence of SEQ ID NO: 19;

amplifying the *Legionella dumoffii* legS2 nucleic acid comprises contacting the sample with a primer consisting of the nucleic acid sequence of SEQ ID NO: 21 and a primer consisting of the nucleic acid sequence of SEQ ID NO: 22;

amplifying the *Legionella feeleii* figA nucleic acid comprises contacting the sample with a primer consisting of the nucleic acid sequence of SEQ ID NO: 24 and a primer consisting of the nucleic acid sequence of SEQ ID NO: 25;

amplifying the *Legionella longbeachae* ligB nucleic acid comprises contacting the sample with a primer consisting of the nucleic acid sequence of SEQ ID NO: 27 and a primer consisting of the nucleic acid sequence of SEQ ID NO: 28; and amplifying the *Legionella micdadei* migB nucleic acid comprises contacting the sample with a primer consisting of the nucleic acid sequence of SEQ ID NO: 30 and a primer consisting of the nucleic acid sequence of SEQ ID NO: 31.

5. The method of claim 1, wherein detecting hybridization between one or more detectably labeled probe and a nucleic acid comprises real-time PCR or quantitative real-time PCR.

6. The method of claim 1, wherein the sample comprises a biological sample or environmental sample.

* * * * *